US008637295B1

(12) United States Patent
Claes et al.

(10) Patent No.: US 8,637,295 B1
(45) Date of Patent: Jan. 28, 2014

(54) PROCESS FOR THE PRODUCTION OF L-LYSINE

(75) Inventors: Wilfried Claes, Bielefeld (DE); Brigitte Bathe, Salzkotten (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/314,162

(22) Filed: Dec. 7, 2011

Related U.S. Application Data

(63) Continuation-in-part of application No. 12/707,668, filed on Feb. 17, 2010, now abandoned.

(60) Provisional application No. 61/202,353, filed on Feb. 20, 2009.

(51) Int. Cl.
*C12N 1/20* (2006.01)
*C12Q 1/68* (2006.01)
*C12N 15/00* (2006.01)
*C12N 9/02* (2006.01)
*C12P 13/08* (2006.01)
*C07H 21/04* (2006.01)
*C07H 21/02* (2006.01)

(52) U.S. Cl.
USPC ....... 435/252.32; 435/6.1; 435/440; 435/189; 435/252.3; 435/320.1; 435/115; 536/23.2; 536/23.1

(58) Field of Classification Search
None
See application file for complete search history.

(56) References Cited

U.S. PATENT DOCUMENTS

| 5,431,933 | A | 7/1995 | Binder et al. | |
|---|---|---|---|---|
| 6,200,785 | B1 * | 3/2001 | Kreutzer et al. | 435/115 |
| 7,332,310 | B2 | 2/2008 | Nakagawa et al. | |

FOREIGN PATENT DOCUMENTS

| AU | 200054213 B2 | 1/2001 |
|---|---|---|
| EP | 0 533 039 A1 | 3/1993 |
| EP | 0 534 865 A1 | 3/1993 |
| EP | 0 607 373 B1 | 3/1997 |
| WO | WO 01/00843 A2 | 1/2001 |

OTHER PUBLICATIONS

Vasicova et al. Analysis of the *Corynebacterium glutamicum* dapA promoter. J Bacteriol. Oct. 1999;181(19):6188-91.*
Amann, et al., "ATG vectors' for regulated high-level expression of cloned genes in *Escherichia coli*," Gene 40:183-190 (1985).
Amann, et al., "Tightly regulated *tac* promoter vectors useful for the expression of unfused proteins in *Escherichia coli*," Gene 69:301-315 (1988).
Chapon, C., "Expression of *malT*, the regulator gene of the maltose regulon in *Escherichia coli*, is limited both at transcription and translation," *EMBO Journal* 1(3):369-374 (1982).
Cremer, et al., "Control of the Lysine Biosynthesis Sequence in *Corynebacterium glutamicum* as Analyzed by Overexpression of the Individual Corresponding Genes," *Applied and Environmental Microbiology* 57(6):1746-1752 (Jun. 1991).
Fournier, et al., "Point Mutation in the Pribnow Box, the Molecular Basis of β-Lactamase Overproduction in *Klebsiella oxytoca*," *Antimicrobial Agents and Chemotherapy* 39(6):1365-1368 (Jun. 1995).
Hawley, et al., "Compilation and analysis of *Escherichia coli* promoter DNA sequences," *Nucleic Acids Research* 11(8):2237-2255 (1983).
Kalinowski, et al., "The complete *Corynebacterium glutamicum* ATCC 13032 genome sequence and its impact on the production of L-aspartate-derived amino acids and vitamins," *Journal of Biotechnology* 104:5-25 (2003).
Nisho, et al., "Comparative Complete Genome Sequence Analysis of the Amino Acid Replacements Responsible for the Thermostability of *Corynebacterium efficiens*," *Genome Research* 13(7):1572-1579 (2003).
Ohnishi, et al., "A novel methodology employing *Corynebacterium glutamicum* genome information to generate a new L-lysine-producing mutant," *Applied Microbiology and Biotechnology* 58:217-223 (2002).
Patek, et al., "Promoters of *Corynebacterium glutamicum*," *Journal of Biotechnology* 104:311-323 (2003).
Patek, et al., "Promoters of *Corynebacterium glutamicum*: cloning, molecular analysis and search for a consensus motif," *Microbiology* 142:1297-1309 (1996).
Rosenberg, et al., "The relationship between function and DNA sequence in an intercistronic regulatory region in phage λ" *Nature* 272:414-423 (Mar. 1978).
Schäfer, et al., "Small mobilizable multi-purpose cloning vectors derived from the *Escherichia coli* plasmids pK18 and pK19: a selection of defined deletions in the chromosome of *Corynebacterium glutamicum*," Gene 145:69-73 (1994).
Schwarzer, et al.," Manipulation of *Corynebacterium glutamicum* by gene disruption and replacement," *Bio/Technology* 9:84-87 (Jan. 1991).
Smith, et al., "Amplification and Modification of Dihydrofolate Reductase in *Escherichia coli*," *Journal of Biological Chemistry* 257(15):9043-9048 (Aug. 1982).
Thompson, et al., "Clustal W: improving the sensitivity of progressive multiple sequence alignment through sequence weighting, position-specific gap penalties and weight matrix choice," *Nucleic Acids Research* 22(22):4673-4680 (1994).
Vašicová, et al., "Analysis of the *Corynebacterium glutamicum* dapA Promoter," *Journal of Bacteriology* 181(19):6188-6191 (Oct. 1999).
Yukawa, et al., "Comparative analysis of the *Corynebacterium glutamicum* group and complete genome sequence of strain R." *Microbiology* 153:1042-1058 (2007).
Sequence for *Corynebacterium glutamicum* ATTC 13032 submitted Apr. 7, 2005.
English language abstract for EP 0 534 865 published Mar. 31, 1993.

* cited by examiner

*Primary Examiner* — Yong Pak
(74) *Attorney, Agent, or Firm* — Law Office of: Michael A. Sanzo, LLC

(57) ABSTRACT

The invention relates to mutants of coryneform bacteria in which genes have been enhanced by the use of a mutated promoter region, and to processes for the production of amino acids using bacteria according to the invention.

26 Claims, 1 Drawing Sheet

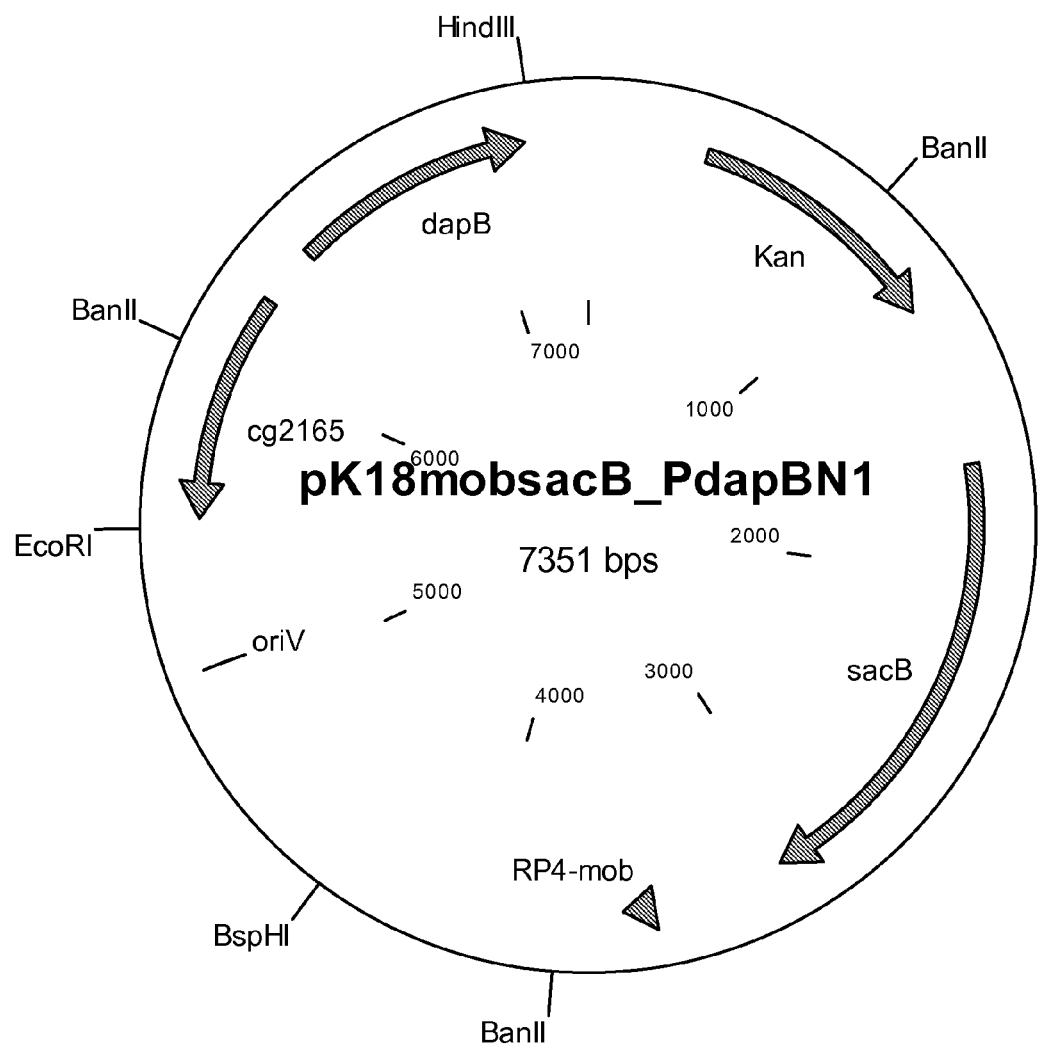

US 8,637,295 B1

PROCESS FOR THE PRODUCTION OF L-LYSINE

CROSS REFERENCE TO RELATED APPLICATIONS

The present application is a continuation-in-part of U.S. application Ser. No. 12/707,668, filed on Feb. 17, 2010, which claims the benefit of U.S. provisional application 61/202,353 filed on Feb. 20, 2009.

FIELD OF THE INVENTION

The invention relates to a process for the production of L-lysine using coryneform bacteria in which genes have been enhanced by using a mutated promoter region.

BACKGROUND OF THE INVENTION

Amino acids are used in human medicine, in the pharmaceuticals industry, in the food industry and very especially in animal nutrition. It is known that amino acids are produced by fermenting strains of coryneform bacteria, in particular *Corynebacterium glutamicum*. Due to their great importance, the production processes are the subject of continuous improvement. Methodological improvements may relate to measures of fermentation technology such as, for example, stirring and oxygen supply, or the composition of the nutrient media such as, for example, the sugar concentration during fermentation, or the work-up to give the product form by, for example, ion exchange chromatography, or the intrinsic performance properties of the microorganism itself.

To improve the performance properties of these microorganisms one uses methods of mutagenesis, selection and mutant selection. In this manner, one obtains strains which are resistant to antimetabolites or which are auxotrophic for important regulatory metabolites and which produce amino acids. A known antimetabolite is the lysine analog S-(2-aminoethyl)-L-cysteine (AEC).

Methods of recombinant DNA technology for the strain improvement of L-lysine-producing strains of *corynebacterium* have also been employed for several years, by amplifying individual amino acid biosynthesis genes and studying the effect on amino acid production. The chromosome of *Corynebacterium glutamicum* has been sequenced completely a while ago (Kalinowski et al., *Journal of Biotechnology* 104:5-25 (2003)). The nucleotide sequence of the genome of *Corynebacterium glutamicum* R has been described in Yukawa et al. (*Microbiology* 153(4):1042-1058 (2007)). The chromosome of *Corynebacterium efficiens* has likewise already been sequenced (Nishio et al., *Genome Res.* 13 (7):1572-1579 (2003)). The relevant sequence information can be found in the public databases. Suitable databases are, for example, the database of the European Molecular Biologies Laboratories (EMBL, Heidelberg, Germany, and Cambridge, UK), the database of the National Center for Biotechnology Information (NCBI, Bethesda, Md., USA), that of the Swiss Institute of Bioinformatics (Swissprot, Geneva, Switzerland), the Protein Information Resource Database (PIR, Washington, D.C., USA) and the DNA Data Bank of Japan (DDBJ, 1111 Yata, Mishima, 411-8540, Japan).

Summarizing reviews of the genetics, the metabolism and the technical importance of *corynebacterium* are found in the papers of Ikeda, of Pfefferle et al. and of Mueller and Huebner in the book "Microbial Production of L-Amino Acids" (*Advances in Biochemical Engineering* 79 (2003), Springer Verlag, Berlin, Germany, editor: T. Scheper), in the special edition "A New Era in *Corynebacterium glutamicum* Biotechnology" of the Journal of Biotechnology (volume 104 (1-3), 2003, editor: A. Pühler and T. Tauch) and in the "Handbook of *Corynebacterium glutamicum*" (editor: L. Eggeling and M. Bott, CRC Press, Taylor & Francis Group, Boca Raton, Fla., USA, 2005).

The nucleotide sequence of the dapB gene which codes for the *Corynebacterium glutamicum* dihydrodipicolinate reductase is publicly available, inter alia, in the database of the National Center for Biotechnology Information (NCBI) of the National Library of Medicine (Bethesda, Md., USA) under the accession number NC_006958 (region: 2051238-2051984 (complementary)) including the upstream and downstream regions. It can furthermore be found in the patent application WO 0100843-A. DapB catalyzes the reduction of 2,3-dihydrodipicolinate to 2,3,4,5-tetrahydrodipicolinate in lysine and diaminopimelate biosynthesis. According to Cremer et al. (*Applied and Environmental Microbiology*, 57(6): 1746-1752 (1991)), the overexpression of dihydrodipicolinate reductase alone does not improve the secretion/excretion of L-lysine.

Gene expression is controlled, inter alia, by the promoter region in the 5' region of a gene. Transcription initiation takes place in the promoter as the result of the interplay between transcription factors and RNA polymerase. This is why a series of conserved sequence motifs are present in promoters which can also be determined in *Corynebacterium glutamicum* (Patek et al., *Microbiology* 142: 1297-1309 (1996)) analogously to the general bacterial promoter elements classified in the best-studied bacterial model organism *Escherichia coli* analogously to the genes transcribed with the aid of the sigma-70 factor (Rosenberg et al., *Nature* 272:414-423 (1978); Hawley and McClure, *Nucleic Acids Research* 11(8):2237-2255 (1983); Fournier et al., *Antimicrobial Agents and Chemotherapy* 39(6):1365-1368 (1995); Chapon, *EMBO Journal* 1:369-374 (1982); Smith et al., *Journal of Bacteriological Chemistry* 257:9043-9048 (1982)):

- the −35 region (the sequence located 35 base pairs upstream of the transcription start), with the consensus sequence: 5'-tttGcca.a-3',
- the −10 region (this sequence is located approximately 10 base pairs upstream of the transcription start), also referred to as Pribnow box, with the consensus sequence: 5'-ggTA.aaT-3'.

The sigma factor of the RNA polymerase which then initiates the transcription of the downstream gene/ORF binds to these two regions. So-called consensus sequences for strong and weak promoters can be deduced from the comparison of the DNA sequences of individual promoters.

The position of the promoter elements relative to one another and/or to the transcription start is of importance, too. The distance of the −10 region to the transcription start is five to seven base pairs in the consensus sequence, the −10 region and the −35 region are 16 to 18 base pairs apart.

The similarity of a promoter with the consensus sequence decides the transcription rate of a gene and thus contributes to the expression level. In *Corynebacterium glutamicum*, the −35 region is markedly less conserved than the −10 region.

If mutations are performed in the regulatory sequence upstream of the start codon, the functionality of these elements as a function of the sequence and of the distances to the start codon must be taken into consideration.

For reasons of clarity, the nucleotide sequence of the coding region (CDS) of the dapB gene coding for the dihydrodipicolinate reductase of *Corynebacterium glutamicum* wild type ("wild-type gene") is shown in SEQ ID NO:1 in accordance with the specifications of the NCBI database and the resulting amino acid sequence of the encoded dihydrodipicolinate reductase is shown in SEQ ID NO:2 and 4. SEQ ID NO:3 additionally shows nucleotide sequences (in each case approximately 1000 nucleotides) which are located upstream and downstream of the CDS.

OBJECT OF THE INVENTION

The inventors have made it their object to provide novel measures for the improved production of L-lysine.

BRIEF DESCRIPTION OF THE DRAWINGS

FIG. 1: Map of plasmid pK18mobsacB_PdapBN1. The abbreviations and names used have the following meanings. The information on the base pair numbers are approximations obtained within the reproducibility of measurements.
Kan: kanamycin resistance gene
BanII: cleavage site of the restriction enzyme BanII
BspHI: cleavage site of the restriction enzyme BspHI
EcoRI: cleavage site of the restriction enzyme EcoRI
PstI: cleavage site of the restriction enzyme PstI
dapB: dapBN1 allele
cg2165: open reading frame cg2165
sacB: sacB gene
RP4-mob: mob region with the replication origin for the transfer (oriT)
oriV: replication origin V

DESCRIPTION OF THE INVENTION

In its broadest aspects, the invention is directed to mutants of coryneform bacteria which comprise a DNA fragment with promoter activity. The DNA fragment has the sequence of SEQ ID NO:12 but with one or more substitutions in the region of positions 36-42 and preferably at positions 36, 37, 40 or 42. The invention also encompasses processes for the fermentative production of L-lysine using the mutants and to isolated polynucleotides comprising sequences corresponding to the promoters.

In more specific, and more preferred, embodiments, the invention relates to a recombinant L-lysine-secreting/excreting coryneform bacterium which comprises an isolated DNA fragment with promoter activity, where the DNA fragment has the sequence SEQ ID NO:12, also shown in SEQ ID NO:3 at positions 916 to 975, with one or more of the substitutions in the promoter region selected from the group consisting of:
  a) substitution of the nucleobase thymine at position 36 of the promoter region of the dapB gene according to SEQ ID NO:12 by guanine,
  b) substitution of the nucleobase cytosine at position 37 of the promoter region of the dapB gene according to SEQ ID NO:12 by guanine,
  c) substitution of the nucleobase guanine at position 40 of the promoter region of the dapB gene according to SEQ ID NO:12 by thymine and
  d) substitution of the nucleobase cytosine at position 42 of the promoter region of the dapB gene according to SEQ ID NO:12 by adenine,
shown in SEQ ID NO:13 and in SEQ ID NO:5 at positions 823 to 882.

It has been found in the work carried out in connection with the present invention that for example the activity of the following DNA fragment with promoter activity from the 5' region of the dapB gene of *Corynebacterium glutamicum*, coding for dihydrodipicolinate reductase, 5'-taggtatgga tat cagcacc ttctgaacgg gtacgtag actggtgggc gtttgaaaaa-3' (SEQ ID NO:12) is enhanced by a t-to-g transversion at position 36, a c-to-g transversion at position 37, a g-to-t transversion at position 40 and a c-to-a transversion at position 42 in the −10 region 5 taggtatgga tatcagcacc ttctgaacgg gtacgggtat aatggtgggc gtttgaaaaa-3' (SEQ ID NO:13). The −35 region, the −10 region and the transcription start are indicated by underlining.

Furthermore included are microorganisms which comprise an isolated DNA fragment with promoter activity wherein the DNA fragment is linked at the 3' end to a second DNA fragment with the nucleotide sequence of position 883 to 912 of SEQ ID NO:5, the naturally occurring 3'-flanking region of the isolated DNA fragment, and microorganisms which comprise an isolated DNA fragment with promoter activity, wherein the DNA fragment at the 5' end is linked to a third DNA fragment with the nucleotide sequence of position 693 to 822 of SEQ ID NO:5, the naturally occurring 5'-flanking region of the isolated DNA fragment.

Preferred microorganisms are those wherein at least one DNA fragment with the nucleotide sequence of position 823 to 912 of SEQ ID NO:5 at the 3' end is operably linked to a polynucleotide coding for an enzyme/protein of the known amino acid biosynthesis pathways or of the amino acid transport or enzymes of the anaplerotic metabolism or enzymes for the production of reduced nicotinamide adenine dinucleotide phosphate or enzymes of the glycolysis or PTS enzymes or enzymes of the sulfur metabolism. The term "operably linked/connected" means that a regulatory sequence such as a promoter governs the expression of a gene. Especially preferred are microorganisms wherein at least one DNA fragment with the nucleotide sequence of position 823 to 912 of SEQ ID NO:5 is operably linked at the 3' end to a polynucleotide coding for a protein with the activity of a dihydrodipicolinate reductase.

The abovementioned recombinant L-lysine-secreting/excreting coryneform bacteria preferably include those in which a polynucleotide which is operably linked is one which codes for a polypeptide whose amino acid sequence is at least 85% or at least 90%, in particular at least 95%, preferably at least 98% or at least 99%, especially preferably 99.6% and very especially preferably 100% identical to an amino acid sequence corresponding to SEQ ID NO:2, where the polypeptide has the activity of a dihydrodipicolinate reductase, comprises essentially a length of 248 amino acids and has been enhanced by one or more of the substitutions in the promoter region selected from the group consisting of:
  a) substitution of the nucleobase thymine at position 36 of the promoter region of the dapB gene according to SEQ ID NO:12 by guanine (T (−55) G mutation),
  b) substitution of the nucleobase cytosine at position 37 of the promoter region of the dapB gene according to SEQ ID NO:12 by guanine (C (−54) G mutation),
  c) substitution of the nucleobase guanine at position 40 of the promoter region of the dapB gene according to SEQ ID NO:12 by thymine (G (−51) T mutation) and
  d) substitution of the nucleobase cytosine at position 42 of the promoter region of the dapB gene according to SEQ ID NO:12 by adenine (C (−49) A mutation).

The substitutions in brackets are numbered in such a way that the number +1 is assigned to nucleotide A of the start codon ATG of the operably linked polynucleotide. Since according to convention the number 0 does not exist, the number −1 is assigned to the nucleotide positioned upstream of the A of the start codon ATG.

Among the coryneform bacteria, the genus *Corynebacterium* is preferred. Among the genus *Corynebacterium*, the following species are preferred: *Corynebacterium efficiens* (type strain DSM44549); *Corynebacterium glutamicum* (type strain ATCC13032); *Corynebacterium thermoaminogenes* (for example strain FERM BP-1539); and *Corynebacterium ammoniagenes* (type strain ATCC6871); with the species *Corynebacterium glutamicum* being very especially preferred.

Some representatives of the species *Corynebacterium glutamicum* are also known by different species names in the prior art. These include, for example: *Corynebacterium acetoacidophilum* ATCC13870; *Corynebacterium lilium* DSM20137; *Corynebacterium melassecola* ATCC17965; *Brevibacterium flavum* ATCC14067; *Brevibacterium lactofermentum* ATCC13869; *Brevibacterium divaricatum* ATCC14020; and *Microbacterium ammoniaphilum* ATCC15354. The term "*Micrococcus glutamicus*" for *Corynebacterium glutamicum* has also been used.

The strains of coryneform bacteria employed for the measures of the invention preferably already have the ability of concentrating the desired amino acid in the cell or of secreting/excreting it into the surrounding nutrient medium and of accumulating it. For this the term "to produce" will also be used hereinbelow. In particular, the strains of coryneform bacteria employed have the ability of concentrating or accumulating ≥(at least) 0.25 g/l, ≥0.5 g/l, ≥1.0 g/l, ≥1.5 g/l, ≥2.0 g/l, ≥4 g/l or ≥10 g/l of the desired amino acid in ≤(a maximum of) 120 hours, ≤96 hours, ≤48 hours, ≤36 hours, ≤24 hours or ≤12 hours in the cell or in the nutrient medium. These may be strains which have been generated by mutagenesis and selection, by recombinant DNA techniques or by a combination of the two methods.

It is obvious and does not require any further explanation that one can also arrive at bacteria according to the invention by first enhancing, in a wild strain, such as, for example, in strain ATCC13032, a gene, preferably the dapB gene, with the aid of the measures of the invention and subsequently causing the bacterium by suitable further genetic measures to produce the desired L-lysine(s).

Known representatives of L-lysine-producing or -secreting/-excreting strains of coryneform bacteria are, for example: *Corynebacterium glutamicum* DM58-1/pDM6 (=DSM4697) described in EP 0 358 940; *Corynebacterium glutamicum* MH20-22B (=DSM16835) described in Menkel et al. (Applied and Environmental Microbiology 55(3), 684-688 (1989)); *Corynebacterium glutamicum* AHP-3 (=Ferm BP-7382) described in EP 1 108 790; *Corynebacterium glutamicum* NRRL B-11474 described in U.S. Pat. No. 4,275,157; and *Corynebacterium thermoaminogenes* AJ12521 (=FERM BP-3304) described in U.S. Pat. No. 5,250,423. Information on the taxonomical classification of strains of this group of bacteria are found, among others, in Seiler (Journal of General Microbiology 129, 1433-1477 (1983)), Kinoshita (1985, Glutamic Acid Bacteria, p 115-142. In: Demain and Solomon (ed), Biology of Industrial Microorganisms. The Benjamin/Cummins Publishing Co., London, UK), Kämpfer and Kroppenstedt (Canadian Journal of Microbiology 42, 989-1005 (1996)), Liebl et al (International Journal of Systematic Bacteriology 41, 255-260 (1991)) and in U.S. Pat. No. 5,250,434.

Strains with the denomination "ATCC" can be obtained from the American Type Culture Collection (Manassas, Va., USA). Strains with the denomination "DSM" can be obtained from the Deutsche Sammlung of Mikroorganismen and Zellkulturen (DSMZ, Brunswick, Germany). Strains with the denomination "NRRL" can be obtained from the Agricultural Research Service Patent Culture Collection (ARS, Peoria, Ill., USA). Strains with the denomination "FERM" can be obtained from the National Institute of Advanced Industrial Science and Technology (AIST Tsukuba Central 6, 1-1-1 Higashi, Tsukuba Ibaraki, Japan).

Chemically, a gene is a polynucleotide. Another term herefor is nucleic acid. At the molecular level, a gene consists of two different regions: (1) a DNA region from which a single-stranded RNA copy is generated by transcription, and (2) all additional DNA segments which are involved in the regulation of this copying process. An allele refers to a possible variant of such a gene.

The prior art also refers to the polypeptide with dihydrodipicolinate reductase activity which is encoded by the dapB gene as "DHDP reductase". In accordance with the IUPAC (International Union of Pure and Applied Chemistry) nomenclature, it has the EC number 1.3.1.26. It catalyzes the reaction:

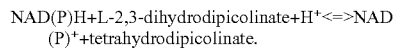

NAD(P)H+L-2,3-dihydrodipicolinate+H⁺<=>NAD(P)⁺+tetrahydrodipicolinate.

The term L-amino acids comprises the proteinogenic amino acids and also L-ornithine and L-homoserine. Proteinogenic L-amino acid is understood as meaning the L-amino acids found in natural proteins, i.e. in proteins of microorganisms, plants, animals and humans. The proteinogenic amino acids include L-aspartic acid, L-asparagine, L-threonine, L-serine, L-glutamic acid, L-glutamine, L-glycine, L-alanine, L-cysteine, L-valine, L-methionine, L-isoleucine, L-leucine, L-tyrosine, L-phenylalanine, L-histidine, L-lysine, L-tryptophan, L-arginine, L-proline and, if appropriate, L-selenocysteine and L-pyrrolysine. Preferred are the L-amino acids L-lysine, L-glutamic acid, L-glutamine, L-arginine, L-proline and L-ornithine. L-lysinee is especially preferred.

The mutants according to the invention preferentially secrete/excrete the abovementioned proteinogenic amino acids, in particular L-lysine. The term amino acids also comprises their salts such as, for example, lysine monohydrochloride or lysine sulfate in the case of the amino acid L-lysine.

The amino acid sequence of the dihydrodipicolinate reductase of coryneform bacteria is at least 85% or at least 90%, preferably at least 95%, especially preferably at least 98% or at least 99% identical to the amino acid sequence of SEQ ID NO:2 and comprises or has essentially a length of 248 amino acids, with a length of 248 amino acids being preferred. The dihydrodipicolinate reductase very especially preferably comprises or has the amino acid sequence of SEQ ID NO:2, where, if appropriate, no more than 5, preferably no more than 2, especially preferably no more than one conservative amino acid exchange(s) may be present in the amino acid sequence of SEQ ID NO:2. The activity of the dihydrodipicolinate reductase is essentially not modified by the conservative amino acid exchanges.

In this context, the term "essentially a length of 248 amino acids" takes into consideration that owing to the insertion or deletion of one (1) or more, but no more than 10, 9, 8, 7, 6, 5, 4, 3 or 2, amino acids within the polypeptide or at the end of N or C terminus of the polypeptide, the length of the encoded polypeptide varies slightly in different types or strains of L-lysine-secreting/excreting coryneform bacteria.

In the case of aromatic amino acids, conservative substitutions are meant to mean that phenylalanine, tryptophan and tyrosine are substituted for one another. In the case of the hydrophobic amino acids, conservative substitutions mean that leucine, isoleucine and valine are substituted for one another. In the case of the polar amino acids, conservative substitutions mean that glutamine and asparagine are substituted from one another. In the case of the basic amino acids, conservative substitutions mean that arginine, lysine and histidine are substituted for one another. In the case of the acidic amino acids, conservative substitutions mean that aspartic acid and glutamic acid are substituted for one another. In the case of the hydroxyl-group-comprising amino acids, conservative substitutions mean that serine and threonine are substituted for one another.

During work carried out in the context of the present invention, comparing the amino acid sequence with the Clustal program (Thompson et al., *Nucleic Acids Research* 22:4637-4680 (1994)) has revealed that the amino acid sequences of the dihydrodipicolinate reductase of various bacteria such as, for example, *Mycobacterium tuberculosis, Bifidobacterium longum, Streptomyces coelicolor, Corynebacterium efficiens, Corynebacterium jeikeium, Corynebacterium glutamicum* R and *Corynebacterium glutamicum* comprise a sequence motif consisting of the sequence Phe-Asp/Glu-Ser-Ala/Val-Glu-Val-Ile/Val-Glu-Leu-His-His-Pro-Asn/Thr/His-Lys-Val/Leu/Ala-Asp-Ala-Pro-Ser-Gly-Thr-Ala (SEQ ID NO:16), a sequence motif consisting of the sequence Val-Asp/Gln-Gly-Ile/Val-Pro/His-Val-His-Ala-Val-Arg-Leu/Met (SEQ ID NO:17) and also a sequence motif consisting of the sequence Val-Leu/Phe-Ile/Val-Ala-Pro-Asn-Phe-Ala/Ser-Ile-Ser/Gly-Ala-Val-Leu (SEQ ID NO:18). The terms "Asp/Glu", "Ala/Val", "Ile/Val" and the like mean that "Asp or Glu" or "Ala or Val" or "Ile or Val" and the like are present at the corresponding position.

Accordingly, preferred mutants of coryneform bacteria are those which comprise a dapB allele which codes for a polypeptide with dihydrodipicolinate reductase enzyme activity which comprises at least one amino acid sequence selected from the group consisting of Phe-Asp/Glu-Ser-Ala/Val-Glu-Val-Ile/Val-Glu-Leu-His-His-Pro-Asn/Thr/His-Lys-Val/Leu/Ala-Asp-Ala-Pro-Ser-Gly-Thr-Ala (SEQ ID NO:16), Val-Asp/Gln-Gly-Ile/Val-Pro/His-Val-His-Ala-Val-Arg-Leu/Met (SEQ ID NO:17) and Val-Leu/Phe-Ile/Val-Ala-Pro-Asn-Phe-Ala/Ser-Ile-Ser/Gly-Ala-Val-Leu (SEQ ID NO:18) and which comprises in the promoter region of the dapB allele at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation).

The amino acid sequence motif Phe-Asp/Glu-Ser-Ala/Val-Glu-Val-Ile/Val-Glu-Leu-His-His-Pro-Asn/Thr/His-Lys-Val/Leu/Ala-Asp-Ala-Pro-Ser-Gly-Thr-Ala (SEQ ID NO:16) is present for example in SEQ ID NO:2 or 4 from position 125 to 146 or at a position of an amino acid sequence which is at least 90% identical and which corresponds to this position of the amino acid sequence. The amino acid sequence motif Val-Asp/Gln-Gly-Ile/Val-Pro/His-Val-His-Ala-Val-Arg-Leu/Met (SEQ ID NO:17) is present for example in SEQ ID NO:2 or 4 from position 181 to 191 or at a position of an amino acid sequence which is at least 90% identical and which corresponds to this position of the amino acid sequence. The amino acid sequence motif Val-Leu/Phe-Ile/Val-Ala-Pro-Asn-Phe-Ala/Ser-Ile-Ser/Gly-Ala-Val-Leu (SEQ ID NO:18) is present for example in SEQ ID NO:2 od 4 from position 101 to 113 or at a position of an amino acid sequence which is at least 90% identical and which corresponds to this position of the amino acid sequence.

It is known that the terminal methionine is removed upon protein synthesis by host enzymes, known as amino peptidases.

The concept "a position which corresponds to a position of the amino acid sequence" or "a position which is comparable to a position of the amino acid sequence" is understood as meaning that insertion or deletion of an amino-acid-encoding codon in the N-terminal region (based on the position of SEQ ID NO:2 or 4) of the encoded polypeptide formally increases the indication of position and length by one unit in the case of an insertion or reduces it by one unit in the case of a deletion. For example, the deletion of the GGA codon, which codes for the amino acid glycine, at position 2 of SEQ ID NO: 2 or 4 means that the L-phenylalanine of position 125 moves to position 124. Equally, the insertion or deletion of an amino-acid-encoding codon in the C-terminal region of the encoded polypeptide formally increases the indication of length by one unit in the case of an insertion or reduces it by one unit in the case of a deletion. Such comparable positions can be identified readily by comparing the amino acid sequences in the form of an alignment, for example with the aid of the Clustal program or of the MAFFT program.

The enzymatic activity is essentially not affected by such insertions and deletions. "Essentially not affected" means that the enzymatic activity of the variants mentioned differs by a maximum of 10%, a maximum of 7.5%, a maximum of 5%, a maximum of 2.5% or a maximum of 1% from the activity of the polypeptide with the amino acid sequence of SEQ ID NO:2 or 4.

Accordingly, the invention also relates to dapB alleles which code for polypeptide variants of SEQ ID NO: 2 or 4 which have one or more insertion(s) or deletion(s) and which comprise, in the promoter region of the dapB allele, at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation). The polypeptide preferably comprises a maximum of 5, a maximum of 4, a maximum of 3 or a maximum of 2 insertions or deletions of amino acids.

The abovementioned sequence motifs Phe-Asp/Glu-Ser-Ala/Val-Glu-Val-Ile/Val-Glu-Leu-His-His-Pro-Asn/Thr/His-Lys-Val/Leu/Ala-Asp-Ala-Pro-Ser-Gly-Thr-Ala ((SEQ ID NO:16), Val-Asp/Gln-Gly-Ile/Val-Pro/His-Val-His-Ala-Val-Arg-Leu/Met ((SEQ ID NO:17) and Val-Leu/Phe-Ile/Val-Ala-Pro-Asn-Phe-Ala/Ser-Ile-Ser/Gly-Ala-Val-Leu (SEQ ID NO:18) are preferably not disrupted by such insertions/deletions.

Traditional in-vivo mutagenesis methods with cell populations of coryneform bacteria using mutagenic substances such as, for example, N-methyl-N'-nitro-N-nitrosoguanidine (MNNG), ethylmethanesulfonate (EMS), 5-bromouracil, or ultraviolet light may be used for generating the promoter region mutations according to the invention. Mutagenesis methods are described for example in Manual of Methods for General Bacteriology (Gerhard et al. (Eds.), American Society for Microbiology, Washington, D.C., USA, 1981) or in Tosaka et al. (*Agricultural and Biological Chemistry* 42(4): 745-752 (1978)) or in Konicek, et al. (*Folia Microbiologica* 33:337-343 (1988)). Typical mutageneses using MNNG comprise concentrations of from 50 to 500 mg/l or else higher concentrations up to a maximum of 1 g/l, an incubation time of from 1 to 30 minutes at pH 5.5 to 7.5. Under these conditions, the number of viable cells is reduced by approximately 50% to 90% or approximately 50% to 99% or approx. 50% to 99.9% or more.

Mutants or cells are removed from the mutagen-treated cell population and multiplied. It is preferred to study, in a further step, their ability of secreting/excreting amino acids, preferably L-lysine, in a batch culture when using a suitable nutrient medium. Suitable nutrient media and test conditions are described, inter alia, in U.S. Pat. No. 6,221,636, in U.S. Pat. No. 5,840,551, in U.S. Pat. No. 5,770,409, in U.S. Pat. No. 5,605,818, in U.S. Pat. No. 5,275,940 and in U.S. Pat. No. 4,224,409. When using suitable automated plants such as, for example, as described in Zimmermann, et al. (VDI Berichte No. 1841, VDI-Verlag, Düsseldorf, Germany 2004, 439-443) or Zimmermann (*Chemie Ingenieur Technik* 77 (4):426-428 (2005)), a large number of mutants can be studied within a short period of time. In general, a maximum of 3000, a maximum of 10 000, a maximum of 30 000 or else a maximum of 60 000 mutants are studied, if appropriate even more. In this manner, mutants which, in comparison with the parent strain or the non-mutagen-treated starting strain, secrete/excrete more amino acids into the nutrient medium, or secrete/excrete more amino acids into the cell itself, are identified. For example, these include mutants whose amino acid secretion is increased by at least 0.5%.

Thereafter, DNA is provided by, or isolated from, the mutants, and the corresponding polynucleotides, preferably including the promoter regions, are synthesized with the aid of the polymerase chain reaction using primer pairs which permit the amplification of the polynucleotides coding for an enzyme/protein of the known amino acid biosynthesis pathways or of the amino acid transport or enzymes of the anaplerotic metabolism or enzymes for the production of reduced nicotinamide adenine dinucleotide phosphate or enzymes of the glycolysis or PTS enzymes or enzymes of the sulfur metabolism.

If appropriate, the entire chromosome of the mutant is determined. Here, it is possible to employ the method described by Margulies, et al. (*Nature* 437(7057):376-380 (2005)) and Velicer, et al. (*Proceedings of the National Academy of Sciences, U.S.A.*: 103(21):8107-8112 (2006)), which is known in expert circles by the keyword "pyro-sequencing" and which makes possible the rapid sequencing of complete genomes.

Thus, the corresponding polynucleotide is synthesized, using, inter alia, primer pairs which permit the amplification of the mutations according to the invention in the promoter region of the dapB allele and, if appropriate, of the dapB gene or dapB allele. It is preferred to isolate the DNA from those mutants which secrete/excrete amino acids in increased quantities.

To this end, it is possible to select any primer pairs from the nucleotide sequence upstream and downstream from the mutation according to the invention, and from the nucleotide sequence which is complementary thereto. In this context, a primer of a primer pair preferably comprises at least 15, at least 18, at least 20, at least 21 or at least 24 successive nucleotides selected from the nucleotide sequence between position 1 and 915 of SEQ ID NO:3. The corresponding second primer of a primer pair comprises at least 15, at least 18, at least 20, at least 21 or at least 24 successive nucleotides selected for example from the complementary nucleotide sequence from position 2702 and 1753 of SEQ ID NO:3.

If it is desired to amplify the promoter region as shown in SEQ ID NO:9, it is preferred to choose the primer pair from the nucleotide sequence between position 850 and 900 of SEQ ID NO:3 and from the complementary nucleotide sequence between position 1056 and 1006 of SEQ ID NO:3. A suitable primer pair is, for example, the primer pair dapB_P_A1 and dapB_P_E1, which is shown as SEQ ID NO:10 and SEQ ID NO:11. Moreover, the primer can feature recognition sites for restriction enzymes, a biotin group or further accessories as they are described in the prior art. The total length of the primer is, in general, a maximum of 30, 40, 50 or 60 nucleotides.

In general, thermostable DNA polymerases are employed for the preparation of polynucleotides by amplification of selected sequences, such as the promoter region according to the invention, from DNA provided, for example chromosomal DNA ("template DNA") by amplification by means of PCR. Examples of such DNA polymerases are the Taq polymerase from *Thermus aquaticus*, which is sold inter alia by Qiagen (Hilden, Germany), the Vent polymerase from *Thermococcus litoralis*, which is sold inter alia by New England Biolabs (Frankfurt, Germany), the Pfu polymerase from *Pyrococcus furiosus*, which is sold inter alia by Stratagene (La Jolla, USA) or the Phusion High Fidelity DNA polymerase, which is sold by New England BioLabs (Frankfurt, Germany). Polymerases with proof-reading activity are preferred. Proof-reading activity means that these polymerases are capable of recognising misincorporated nucleotides and remedying the mistake by repolymerization (Lottspeich and Zorbas, Bioanalytik, Spektrum Akademischer Verlag, Heidelberg, Germany (1998)). Examples of polymerases with proof-reading activity are the Vent polymerase and the Pfu polymerase.

The conditions in the reaction mixture are adjusted as specified by the manufacturer. In general, the polymerases are provided by the manufacturer together with the customary buffer, which usually has concentrations of 10-100 mM Tris/HCl and 6-55 mM KCl at pH 7.5-9.3. If magnesium chloride is not present in the buffer provided by the manufacturer, it is added at a concentration of 0.5-10 mM. Furthermore, deoxynucleoside triphosphates are added to the reaction mixture at a concentration of 0.1-16.6 mM. The primers are provided into the reaction mixture at a final concentration of 0.1-3 µM and the template DNA optimally at $10^2$ to $10^5$ copies. It is also possible to employ $10^6$ to $10^7$ copies. The relevant polymerase is added to the reaction mixture in an amount of 2-5 units. A typical reaction mixture has a volume of 20-100 µl.

Further additions which may be added to the reaction are bovine serum albumin, Tween-20, gelatin, glycerol, formamide or DMSO (Dieffenbach and Dveksler, PCR Primer—A Laboratory Manual, Cold Spring Harbor Laboratory Press, USA 1995).

A typical PCR course consists of three different, successively repeating temperature steps. First, the reaction is started with increasing the temperature to 92° C.-98° C. for 4 to 10 minutes in order to denature the provided DNA. Then, repeating in the following follow: first a step of 10-60 seconds at approximately 92-98° C. for denaturing the DNA provided, then a step of 10-60 seconds at a certain primer-dependent temperature (annealing temperature), which, as experience has shown, is from 50° C. to 60° C. and which can be calculated specifically for each primer pair, for binding the primers to the DNA provided. The skilled worker will find detailed information in this context in Rychlik et al. (Nucleic Acids Research 18 (21): 6409-6412). This is followed by a synthesis step for elongating the primers provided (extension) at the activity optimum specified in each case for the polymerase, usually in the range of from 73° C. to 67° C., preferably from 72° C. to 68° C., depending on the polymerase. The duration of this extension step depends on the performance of the polymerase and the length of the PCR product to be amplified. In a typical PCR, this step takes 0.5-8 minutes, preferably 2-4 minutes. These three steps are repeated 30 to 35 times, if appropriate up to 50 times. A final extension step of 4-10 minutes terminates the reaction. The polynucleotides generated in this manner are also referred to as amplificates; the term nucleic acid fragment is also customary.

Further instructions and information on PCR is found by the skilled worker for example in the textbook "PCR-Strategies" (Innis, Felfand and Sninsky, Academic Press, Inc., 1995), in the textbook by Diefenbach and Dveksler "PCR Primer—a laboratory manual" (Cold Spring Harbor Laboratory Press, 1995), in the manual Gait "Oligonucleotide synthesis: A Practical Approach" (IRL Press, Oxford, UK, 1984) and in Newton and Graham "PCR" (Spektrum Akademischer Verlag, Heidelberg, Germany, 1994).

The nucleotide sequence is then determined for example by the chain temination method of Sanger et al. (*Proceedings of the National Academies of Sciences, U.S.A.*, 74:5463-5467 (1977)) with the modifications detailed by Zimmermann et al. (*Nucleic Acids Research* 18:1067 pp (1990)) and the polypeptide encoded by this nucleotide sequence is analyzed in particular with regard to the promoter sequence and the amino acid sequence. For the purpose of the latter, the nucleotide sequence is inputted into a program for translating the DNA sequence into an amino acid sequence. Suitable programs are, for example, the program "Patentin", which is available from patent offices, for example the US Patent Office (USPTO) or the "Translate Tool", which is available on the ExPASy Proteomics Server on the World Wide Web (Gasteiger, et al., *Nucleic Acids Research* 31:3784-3788 (2003)).

In this manner, one may identify mutants whose dapB alleles code for polypeptides with dihydrodipicolinate reductase enzyme activity, where in the promoter region of the dapB allele, at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) is present.

Accordingly, the invention relates to a mutant of a coryneform bacterium, which mutant is obtainable by the following steps:
a) treatment, with a mutagenic agent, of a coryneform bacterium with the capability of secreting/excreting amino acids,
b) isolation and growing of the mutant generated in a),
c) preferably determination of the capability of the mutant of excreting in a medium, or of accumulating within the cell, at least 0.5% more amino acid than the coryneform bacterium employed in a),
d) providing nucleic acid from the mutant obtained in b),
e) generation of a nucleic acid molecule (or amplificate or nucleic acid fragment) using the polymerase chain reaction, the nucleic acid of d) and a primer pair consisting of a first primer comprising at least 15 consecutive nucleotides selected from the nucleotide sequence between position 1 and 900, preferably 850 to 900, of SEQ ID NO:3 and a second primer comprising at least 15 consecutive nucleotides selected from the complementary nucleotide sequence between position 2300 and 1006, preferably 1056 and 1006 of SEQ ID NO:3,
f) determination of the nucleotide sequence of the nucleic acid molecule obtained in e), of the promoter region and, if appropriate, determination of the encoded amino acid sequence,
g) if appropriate, comparison of the nucleotide sequence determined in f) with SEQ ID NO:3, and
h) identification of a mutant which comprises a polynucleotide which comprises, in the promoter region of the dapB allele, at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation).

The mutants generated in this manner typically comprise one (1) copy of the above-described dapB allele with the promoter region according to the invention.

By way of example, SEQ ID NO:5 shows the coding region in addition to the nucleotide sequences positioned upstream and downstream of the CDS (in each case approximately 1000 nucleotides), including the promoter region of the dapB allele of a mutant according to the invention. The corresponding region of the wild-type gene is shown as SEQ ID NO:3. SEQ ID NO:3 comprises cytosine at position −49, guanine at position −51, cytosine at position −54 and thymine at position −55. SEQ ID NO:5 comprises adenine at position −49, thymine at position −51, guanine at position −54 and guanine at position −55.

Moreover the nucleotide sequence shown in SEQ ID NO:5 may comprise further base substitutions which are the result of the mutagenesis treatment, but which do not manifest themselves in an altered amino acid sequence. Expert circles also refer to such mutations as silent or neutral mutations. These silent mutations may also already be present in the coryneform bacterium employed for the mutagenesis treatment.

The coryneform bacteria used for the mutagenesis preferably already have the ability of excreting the desired amino acid into the nutrient medium or fermentation liquor surrounding them or of accumulating it within the cell.

L-lysine-producing coryneform bacteria typically have a feedback-resistant or desensitized aspartate kinase. Feedback-resistant aspartate kinases are understood as meaning aspartate kinases (LysC) which, in comparison with the wild form, are less sensitive to inhibition by mixtures of lysine and threonine or mixtures of AEC (aminoethylcysteine) and threonine or lysine alone or AEC alone. The genes or alleles coding for these aspartate kinases which are desensitized in comparison with the wild type are also referred to as lysC$^{FBR}$ alleles. The prior art describes a large number of lysC$^{FBR}$ alleles which code for asparate kinase variants which feature amino acid substitutions in comparison with the wild-type protein. The coding region of the wild type lysC gene of *Corynebacterium glutamicum* corresponding to the accession number AX756575 of the NCBI database is shown in SEQ ID NO:14, and the polypeptide encoded by this gene in SEQ ID NO:15. The amino acid sequence of the wild form of the aspartate kinase varies slightly between different wild-type strains of *Corynebacterium glutamicum*. Thus, the aspartate kinase of the wild-type strain *Corynebacterium glutamicum* ATCC 14067 comprises alanine at position 317. The wild-type aspartate kinase of strain ATCC 13032 comprises serine at this position, as shown in SEQ ID NO:15.

The L-lysine-producing coryneform bacteria employed for the measures of the invention preferably feature a lysC allele which codes for an aspartate kinase variant which has the amino acid sequence of SEQ ID NO:15, the latter comprising one or more of the amino acid substitutions selected from the group consisting of:
LysC A279T (substitution of L-alanine at position 279 of the encoded aspartate kinase protein as shown in SEQ ID NO:15 by L-threonine; see U.S. Pat. No. 5,688,671 and accession numbers E06825, E06826, E08178 and 174588 to 174597),
LysC A279V (substitution of L-alanine at position 279 of the encoded apartate kinase protein as shown in SEQ ID NO:15 by L-valine, see JP 6-261766 and accession number E08179),
LysC L297Q (substitution of L-leucine at position 297 of the encoded asparate kinase protein as shown in SEQ ID NO:15 by L-glutamine; see DE 102006026328, LysC S301F (substitution of L-serine at position 301 of the encoded asparate kinase protein as shown in SEQ ID NO:15 by L-phenylalanine; see U.S. Pat. No. 6,844,176 and accession number E08180), LysC S301Y (substitution of L-serine at position 301 of the encoded asparate kinase protein as shown in SEQ ID NO:15 by L-tyrosine, see Kalinowski et al. (Molecular and General Genetics 224, 317-324 (1990)) and accession number X57226), LysC T308I (substitution of L-threonine at position 308 of the encoded asparate kinase protein as shown in SEQ ID NO:15 by L-isoleucine; see JP 6-261766 and accession number E08181)

LysC T311I (substitution of L-threonine at position 311 of the encoded asparate kinase protein as shown in SEQ ID NO:15 by L-isoleucine; see WO 00/63388 and U.S. Pat. No. 6,893,848), LysC R320G (substitution of L-arginine at position 320 of the encoded asparate kinase protein as shown in SEQ ID NO:15 by glycine; see Jetten et al. (Applied Microbiology and Biotechnology 43, 76-82 (995)) and accession number L27125), LysC G345D (substitution of glycine at position 345 of the encoded asparate kinase protein as shown in SEQ ID NO:15 by -aspartic acid; see Jetten et al. (Applied Microbiology and Biotechnology 43, 76-82 (995)) and accession number L16848), LysC T380I (substitution of L-threonine at position 380 of the encoded asparate kinase protein as shown in SEQ ID NO:15 by L-isoleucine; see WO 01/49854 and accession number AX192358), and LysC S381F (substitution of L-serine at position 381 of the encoded asparate kinase protein as shown in SEQ ID NO:15 by L-phenylalanine; see EP 0435132), where, if appropriate, L-alanine is present at Postion 317 instead of L-serine.

Especially preferred are the lysC$^{FBR}$ allele lysC T311I (substitution of threonine at position 311 of the encoded asparate kinase protein as shown in SEQ ID NO:15 by isoleucine) and a lysC$^{FBR}$ allele comprising at least one substitution selected from the group consisting of A279T (substitution of alanine at position 279 of the encoded asparate kinase protein as shown in SEQ ID NO:15 by threonine), S381F (substitution of serine at position 381 of the encoded asparate kinase protein as shown in SEQ ID NO:15 by phenylalanine), where, if appropriate, the serine at position 317 is substituted by alanine (S317A). Very particularly preferred is the lysC$^{FBR}$ allele lysC T311I (substitution of threonine at position 311 of the encoded asparate kinase protein as shown in SEQ ID NO:15 by isoleucine), where, if appropriate, the serine at position 317 is substituted by alanine (S317A).

Strain DSM 16833 (WO 06/063660) has a lysC$^{FBR}$ allele which codes for an aspartate kinase protein which comprises the amino acid substitution T311I. Strain NRRL B-11474 (U.S. Pat. No. 4,275,157) has a lysC$^{FBR}$ allele which codes for an aspartate kinase protein which comprises the amino acid substitutions A279T and S381F.

Departing from strain DSM17576 and proceeding in the manner described above, a mutant referred to as DM1729_mut#3.2e was isolated which comprises a dapB allele coding for a polypeptide with dihydrodipicolinate reductase enzyme activity, where at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) is present in the promoter region of the dapB allele. The nucleotide sequence of the promoter region of the dapB allele of mutant DM1729_mut#3.2e is shown as SEQ ID NO:5 or 9 or 13.

Moreover, it is possible to use L-lysine-secreting/excreting coryneform bacteria which have properties as they are known from the prior art.

The mutants obtained show a secretion/excretion, or production of the desired amino acid in a fermentation process which is increased in comparison with the starting strain or parent strain employed.

The invention also includes isolated polynucleotides comprising the sequence of SEQ ID NO:12 but with one or more substitutions in the region of positions 36-42 and preferably at positions 36, 37, 40 and 42. Most preferably, the invention relates to an isolated polynucleotide, where the DNA fragment has the sequence SEQ ID NO:12, also shown in SEQ ID NO:3 at positions 916 to 975, with one or more of the substitutions in the promoter region selected from the group consisting of:

e) substitution of the nucleobase thymine at position 36 of the promoter region as shown in SEQ ID NO:12 by guanine, f) substitution of the nucleobase cytosine at position 37 of the promoter region as shown in SEQ ID NO:12 by guanine, g) substitution of the nucleobase guanine at position 40 of the promoter region as shown in SEQ ID NO:12 by thymine and h) substitution of the nucleobase cytosine at position 42 of the promoter region as shown in SEQ ID NO:12 by adenine, shown in SEQ ID NO:13 and in SEQ ID NO:5 at positions 823 to 882.

It furthermore includes an isolated polynucleotide, wherein the described DNA fragment is linked at the 3' end to a second DNA fragment with the nucleotide sequence of position 883 to 912 of SEQ ID NO:5, the naturally occurring 3'-flanking region of the isolated DNA fragment, and an isolated polynucleotide, wherein the described DNA fragment is linked at the 5' end to a third DNA fragment with the nucleotide sequence of position 693 to 822 of SEQ ID NO:5, the naturally occurring 5'-flanking region of the isolated DNA fragment.

Preferred is an isolated polynucleotide wherein at least one DNA fragment with the nucleotide sequence of position 823 to 912 of SEQ ID NO:5 is linked operably at the 3' end to a polynucleotide coding for an enzyme/protein of the known amino acid biosynthesis pathways or of the amino acid transport or enzymes of the anaplerotic metabolism or enzymes for the production of reduced nicotinamide adenine dinucleotide phosphate or enzymes of glycolysis or PTS enzymes or enzymes of the sulfur metabolism.

The term "operably linked/connected" which is used herein means that a regulatory sequence such as a promoter governs the expression of a gene.

Especially preferred is an isolated polynucleotide wherein at least one DNA fragment with the nucleotide sequence of position 823 to 912 of SEQ ID NO:5 is operably linked at the 3' end to a polynucleotide coding for a protein with the activity of a dihydrodipicolinate reductase.

The invention also relates to an isolated polynucleotide which codes for a polypeptide with dihydrodipicolinate reductase enzyme activity, where at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) is present in the promoter region of the dapB gene.

The polynucleotide according to the invention can be isolated from a mutant according to the invention.

It is furthermore possible to employ in-vitro methods for the mutagenesis of the dapB promoter region. When using in-vitro methods, isolated polynucleotides which comprise a dapB allele of a coryneform bacterium including the promoter region, preferably the wild-type allele of *Corynebacterium glutamicum*, which allele is described in the prior art, are subjected to a mutagenic treatment.

The isolated polynucleotides may, for example, be isolated total DNA or chromosomal DNA or else amplificates of at least the promoter region according to the invention which have been prepared with the aid of the polymerase chain reaction (PCR). Such amplificates are also referred to as PCR products. The skilled worker will find instructions on the amplification of DNA sequences with the aid of the polymerase chain reaction in, inter alia, the textbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994). It is also possible to incorporate the promoter region, or the dapB gene with the accompanying promoter region, to be mutagenized first into a vector, for example a bacteriophage or a plasmid.

Suitable methods for the in-vitro mutagenesis are, inter alia, the treatment with hydroxylamine as described by Miller (Miller, J. H.: A Short Course in Bacterial Genetics. A Laboratory Manual and Handbook for *Escherichia coli* and Dap-Bated Bacteria, Cold Spring Harbor Laboratory Press, Cold Spring Harbor, 1992), the use of mutagenic oligonucleotides (T. A. Brown: Gentechnologie für Einsteiger [Genetic engineering for novices], Spektrum Akademischer Verlag, Heidelberg, 1993 and R. M. Horton: PCR-Mediated Recombination and Mutagenesis, Molecular Biotechnology 3, 93-99 (1995)) and the use of a polymerase chain reaction using a DNA polymerase with a high error rate. Such a DNA polymerase is, for example, the Mutazyme DNA polymerase (GeneMorph PCR mutagenesis kit, No. 600550) from Stratagene (LaJolla, Calif., USA).

Further instructions for, and reviews on, the generation of mutations in vivo or in vitro can be found in the prior art and in known textbooks of genetics and molecular biology such as, for example, the textbook by Knippers ("Molekulare Genetik" [Molecular Genetics], 6$^{th}$ edition, Georg Thieme Verlag, Stuttgart, Germany, 1995), that of Winnacker ("Gene and Klone" [Genes and Clones], VCH Verlagsgesellschaft, Weinheim, Germany, 1990) or that of Hagemann ("Allgemeine Genetik" [General Genetics], Gustav Fischer Verlag, Stuttgart, 1986).

The invention furthermore relates to an isolated polynucleotide which codes for a polypeptide with dihydrodipicolinate reductase enzyme activity and which comprises the nucleotide sequence of SEQ ID NO:5, where at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) is present in the promoter region of the dapB allele.

The invention furthermore relates to an isolated polynucleotide which codes for a polypeptide with dihydrodipicolinate reductase enzyme activity and which comprises an amino acid sequence with a length of 248 amino acids and where at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) is present in the promoter region of the dapB allele.

The invention furthermore relates to an isolated polynucleotide which codes for a polypeptide with dihydrodipicolinate reductase enzyme activity, where at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) is present in the promoter region of the dapB allele, where the allele comprises a nucleotide sequence which is identical to the nucleotide sequence of a polynucleotide which is obtainable by a polymerase chain reaction (PCR) using a primer pair whose nucleotide sequences comprise in each case at least 15 consecutive nucleotides which are selected from the nucleotide sequence between position 1 and 900 of SEQ ID NO:3 and from the complementary nucleotide sequence between position 2702 and 1753 of SEQ ID NO:3. An example of such a primer pair is shown in SEQ ID NO:7 and SEQ ID NO:8. The preferred starting material (template DNA) is the chromosomal DNA of coryneform bacteria, which have been treated in particular with a mutagen. The chromosomal DNA of the genus *Corynebacterium* is especially preferred, and that of the species *Corynebacterium glutamicum* is very especially preferred.

The invention furthermore relates to an isolated polynucleotide which hybridizes under stringent conditions with the nucleotide sequence which is complementary to SEQ ID NO:5 and which codes for a polypeptide with dihydrodipicolinate reductase enzyme activity, where at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) is present in the promoter region of the dapB allele.

The skilled worker will find instructions for the hybridization of nucleic acids or polynucleotides in, inter alia, the handbook "The DIG System Users Guide for Filter Hybridization" from Boehringer Mannheim GmbH (Mannheim, Germany, 1993) and in Liebl et al. (*International Journal of Systematic Bacteriology* 41:255-260 (1991)). The hybridization takes place under stringent conditions, this means that only hybrids in which the probe, i.e. a polynucleotide comprising the nucleotide sequence which is complementary to SEQ ID NO:5, and the target sequence, i.e. the polynucleotides identified or treated with the probe, up to at least 90% identical are formed. It is known that the stringency of the hybridization including the wash steps is influenced, or determined, by varying the buffer composition, the temperature and the salt concentration. The hybridization reaction is generally carried out at a relatively low stringency in comparison with the wash steps (Hybaid Hybridisation Guide, Hybaid Limited, Teddington, UK, 1996).

To carry out the hybridization reaction, it is possible, for example, to employ a buffer corresponding to 5×SSC buffer at a temperature of approximately 50° C.-68° C. Here, probes can also hybridize with polynucleotides with less than 90% identity to the nucleotide sequence of the probe employed. Such hybrids are less stable and are removed by washing under stringent conditions. This can be achieved for example by lowering the salt concentration to 2×SSC, followed, if appropriate, by 0.5×SSC (The DIG System User's Guide for Filter Hybridisation, Boehringer Mannheim, Mannheim, Germany, 1995), with a temperature of approx. 50° C.-68° C., approx. 52° C.-68° C., approx. 54° C.-68° C., approx. 56° C.-68° C., approx. 58° C.-68° C., approx. 60° C.-68° C., approx. 62° C.-68° C., approx. 64° C.-68° C., approx. 66° C.-68° C. being set. Temperature ranges of approx. 64° C.-68° C. or approx. 66° C.-68° C. are preferred. If appropriate, it is possible to lower the salt concentration down to a concentration corresponding to 0.2×SSC or 0.1×SSC. If appropriate, the SSC buffer comprises sodium dodecyl sulfate (SDS) in a concentration of 0.1%. By stepwise increasing the hybridization temperature in steps of approx. 1-2° C. from 50° C. to 68° C., it is possible to isolate polynucleotide fragments which have at least 90% or at least 91%, preferably at least 92% or at least 93% or at least 94% or at least 95% or at least 96% and very especially preferably at least 97% or at least 98% or at least 99% identity to the sequence or to the complementary sequence of the probe employed and which code for a polypeptide with dihydrodipicolinate reductase enzyme activity, where at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) is present in the promoter region of the dapB allele. The nucleotide sequence of the polynucleotide obtained in this manner is determined by known methods. Further instructions on the hybridization are commercially available in the form of so-called kits (for example DIG Easy Hyb from Roche Diagnostics GmbH, Mannheim, Germany, Catalog No. 1603558). The nucleotide sequences obtained thus code for polypeptides with dihydrodipicolinate reductase enzyme activity which are at least 90% preferably at least 92% or at least 94% or at least 96%, and very especially preferably at least 97% or at least 98% or at least 99% identical to the amino acid sequence of SEQ ID NO:2 or SEQ ID NO:4.

Furthermore preferred are those isolated polynucleotides which code for a polypeptide with dihydrodipicolinate reductase enzyme activity, where at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) is present in the promoter region of the dapB allele and which comprise at least one sequence motif or one amino acid sequence selected from the group consisting of Phe-Asp/Glu-Ser-Ala/Val-Glu-Val-Ile/Val-Glu-Leu-His-His-Pro-Asn/Thr/His-Lys-Val/Leu/Ala-Asp-Ala-Pro-Ser-Gly-Thr-Ala (SEQ ID NO:16), Val-Asp/Gln-Gly-Ile/Val-Pro/His-Val-His-Ala-Val-Arg-Leu/Met (SEQ ID NO:17) and Val-Leu/Phe-Ile/Val-Ala-Pro-Asn-Phe-Ala/Ser-Ile-Ser/Gly-Ala-Val-Leu (SEQ ID NO:18). The terms "Asp/Glu", "Ala/Val", "Ile/Val" etc. mean that "Asp or Glu" or "Ala or Val" or "Ile or Val" etc. are present at the corresponding position.

The invention furthermore relates to an isolated polynucleotide which codes for a polypeptide with dihydrodipicolinate reductase enzyme activity which comprises the amino acid sequence of SEQ ID NO:2 or SEQ ID NO:4, where at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) is present in the promoter region of the dapB allele. If appropriate, the encoded polypeptide comprises one (1) or more conservative amino acid exchange(s). Preferably, the polypeptide comprises no more than two (2), no more than three (3), no more than four (4) or no more than five (5) conservative amino acid exchanges.

The invention furthermore relates to an isolated polynucleotide which codes for a polypeptide with dihydrodipicolinate reductase enzyme activity which comprises the amino acid sequence of SEQ ID NO:2 or SEQ ID NO:4, including an extension at the N or C terminus by at least one (1) amino acid where at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) is present in the promoter region of the dapB allele. This extension amounts to no more than 50, 40, 30, 20, 10, 5, 3 or 2 amino acids or amino acid residues.

Finally, the invention also relates to dapB alleles which code for polypeptide variants of SEQ ID NO:2 or SEQ ID NO:4 which comprise one or more insertions or deletions, where at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) is present in the promoter region of the dapB allele. They preferably comprise no more than 5, no more than 4, no more than 3 or no more than 2 insertions or deletions of amino acids. The sequence motifs Phe-Asp/Glu-Ser-Ala/Val-Glu-Val-Ile/Val-Glu-Leu-His-His-Pro-Asn/Thr/His-Lys-Val/Leu/Ala-Asp-Ala-Pro-Ser-Gly-Thr-Ala (SEQ ID NO:16), Val-Asp/Gln-Gly-Ile/Val-Pro/His-Val-His-Ala-Val-Arg-Leu/Met (SEQ ID NO:17) or Val-Leu/Phe-Ile/Val-Ala-Pro-Asn-Phe-Ala/Ser-Ile-Ser/Gly-Ala-Val-Leu (SEQ ID NO:18) are preferably not disrupted by such insertions/deletions.

The invention furthermore also relates to an isolated polynucleotide which comprises the nucleotide sequence of SEQ ID NO:5 or 9 or 13.

Finally, the invention relates to an isolated polynucleotide comprising the dapB allele including the promoter region of the mutant DM1729_mut#3.2e.

The isolated polynucleotides according to the invention can be used for generating recombinant strains of microorganisms which, in comparison with the original or parent strain, excrete in an improved manner amino acids into the medium surrounding them or accumulate them within the cell.

A widely used method of incorporating mutations into genes of coryneform bacteria is the allele substitution method, also known as gene replacement. In this method, a DNA fragment which comprises the mutation of interest is transferred into the desired strain of a coryneform bacterium and the mutation is incorporated into the chromsome of the desired strain by at least two recombination events, or crossover events, or the sequence, of a gene, present in the strain in question is replaced by the mutated sequence.

Schwarzer and Pühler (*Bio/Technology* 9:84-87 (1991) have used this method for incorporating a lysA allele which carried a deletion and a lysA allele which carried an insertion into the chromosome of *C. glutamicum* instead of the wild-type gene. Schafer et al. (*Gene* 145:69-73 (1994)) have employed this method for incorporating a deletion into the hom-thrB operon of *C. glutamicum*. Nakagawa et al. (EP 1108790) and Ohnishi et al. (*Applied Microbiology and Biotechnology* 58(2):217-223 (2002)) have employed this method for incorporating various mutations into the chromosome of *C. glutamicum*, departing from the isolated alleles. In this manner, Nakagawa et al. have successfully incorporated a mutation, referred to as Val59Ala, into the homoserine dehydrogenase gene (hom), a mutation referred to as Thr311Ile into the aspartate kinase gene (lysC or ask), a mutation referred to as Pro458Ser into the pyruvate carboxylase gene (pyc) and a mutation referred to as Ala213Thr into the glucose 6-phoshate dehydrogenase gene (zwf) of *C. glutamicum* strains.

In this method, the DNA fragment comprising the mutation of interest is typically present in a vector, in particular a plasmid, which is preferably replicated by the strain to be provided with the mutation to a limited extent only or not at all. In general, it is preferred to use a bacterium of the genus *Escherichia*, preferably of the species *Escherichia coli*, as auxiliary or intermediate host in which the vector is capable of replication.

Examples of such plasmid vectors are the vectors pK*mob and pK*mobsacB described by Schäfer et al. (*Gene* 145:69-73 (1994)), such as, for example, pK18mobsacB, and the vectors described in WO 02/070685 and WO 03/014362. These are capable of replication in *Escherichia coli*, but not in coryneform bacteria. Especially suitable vectors are those which comprise a conditionally negative-dominant acting gene such as, for example, the sacB gene (levan sucrase gene) of, for example, *Bacillus* or the galK gene (galactose kinase gene) of, for example, *Escherichia coli*. (A conditionally negative-dominant acting gene is understood as meaning a gene which, under certain conditions, is disadvantageous for, for example toxic to, the host, but which, under different conditions, has no negative effects on the host which carries the gene.) These make possible the selection for recombination events in which the vector is eliminated from the chromosome. Furthermore, Nakamura et al. (U.S. Pat. No. 6,303, 383) have described a temperature-sensitive plasmid for coryneform bacteria which is only capable of replication at temperatures below 31° C.

Thereafter, the vector is transferred into the coryneform bacteria by conjugation, for example following the method of Schäfer (*Journal of Bacteriology* 172:1663-1666 (1990)) or by transformation, for example by the method of Dunican and Shivnan (*Bio/Technology* 7:1067-1070 (1989)) or by the method of Thierbach et al. (*Applied Microbiology and Biotechnology* 29:356-362 (1988)). If appropriate, the DNA transfer can also be accomplished by particle bombardment.

Following homologous recombination by means of a first, integration-causing crossover and a suitable second, excision-causing crossover event in the target gene or the target sequence, the incorporation of the mutation is accomplished and a recombinant bacterium is obtained.

Methods which can be employed for the identification and characterization of the strains obtained are, inter alia, the methods of Southern blotting hybridization, polymerase chain reaction, sequence analysis, the method of the "Fluorescence Resonance Energy Transfer" (FRET) (Lay et al., *Clinical Chemistry* 43:2262-2267 (1997)) or enzymological methods.

Accordingly, the invention furthermore relates to a process for generating a coryneform bacterium in which
  a) a polynucleotide according to the invention is transferred into a coryneform bacterium,
  b) a promoter region which is present in the chromosome of the coryneform bacteria is substituted by the polynucleotide of a) which contains guanine at position 36, guanine at position 37, thymine at position 40 and adenine at position 42, and
  c) the coryneform bacterium obtained in steps a) and b) is multiplied.

Accordingly, the invention furthermore relates to a process for generating a coryneform bacterium in which
  a) a polynucleotide according to the invention is transferred into a coryneform bacterium,
  b) the dihydrodipicolinate reductase gene which is present in the chromosome of the coryneform bacterium whose promoter region comprises cytosine at position −49, guanine at position −51, cytosine at position −54 and thymine at position −55, is substituted by the polynucleotide of a) which contains adenine at position −49, thymine at position −51, guanine at position −54 and guanine at position −55, and
  c) the coryneform bacterium obtained in steps a) and b) is multiplied.

In this manner, a recombinant coryneform bacterium is obtained which comprises one (1) dapB promoter region according to the invention instead of the wild-typ dapB promoter region.

In this manner, a recombinant microorganism is obtained which comprises at least one (1) copy or more than one copy of a promoter region according to the invention where a substitution of thymine by guanine is present at position 36, a substitution of cytosine by guanine is present at position 37, a substitution of guanine by thymine is present at position 40 and a substitution of cytosine by adenine is present at position 42 in the promoter region.

Equally, a recombinant microorganism is preferably obtained in this manner which comprises at least one (1) copy or more than one copy of a polynucleotide according to the invention which codes for a dihydrodipicolinate reductase, where at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) is present in the promoter region of the dapB allele.

Accordingly, the invention furthermore relates to hosts or host cells, preferably microorganisms, especially preferably coryneform bacteria and bacteria of the genus *Escherichia* which comprise the polynucleotides according to the invention. Equally, the invention relates to microorganisms which are generated using the isolated polynucleotides. Such microorganisms or bacteria are also referred to as recombinant microorganisms or recombinant bacteria. Equally, the invention relates to vectors which comprise the polynucleotides according to the invention. Finally, the invention also relates to hosts which comprise these vectors.

The invention furthermore relates to microorganisms which feature inside their cell an increased concentration or activity of the dihydrodipicolinate reductase variants according to the invention. In addition, it may be advantageous for the improved production of L-lysine to overexpress various genes in the mutants or recombinant strains according to the invention.

In general, the use of endogenous genes is preferred. "Endogenous genes" or "endogenous nucleotide sequences" are understood as meaning the genes or nucleotide sequences or alleles which are present in the population of a species.

Thus, it is possible to overexpress, for the production of L-lysine, one or more of the genes selected from the group consisting of:
  a gene dapA which codes for a dihydrodipicolinate synthase (DapA, EC No. 4.2.1.52), such as, for example, the dapA gene from the wild type of *Corynebacterium glutamicum*, which gene is described in EP 0 197 335,
  a lysA gene which codes for a diaminopimelate decarboxylase (LysA, EC No. 4.1.1.20), such as, for example, the lysA gene of *Corynebacterium glutamicum* ATCC13869, which gene is described in U.S. Pat. No. 6,090,597, a zwf gene which codes for a glucose 6-phosphate dehydrogenase (Zwf, EC No. 1.1.1.49), such as, for example, the zwf gene of the wild type of *Corynebacterium glutamicum*, which gene is described in JP-A-09224661 and EP-A-1108790, the zwf alleles of *Corynebacterium glutamicum*, which alleles are described in US-2003-0175911-A1 and which code for a protein with glucose 6-phosphate dehydrogenase activity, where, for example, the L-alanine at position 243 of the amino acid sequence is substituted by L-threonine or in which the L-aspartic acid at position 245 is substituted by L-serine, a pyc gene which codes for a pyruvate carboxylase (Pyc, EC No. 6.4.1.1), such as, for example, the pyc gene of the wild type of *Corynebacterium glutamicum*, which gene is described, for example, in DE-A-198 31 609 and EP 1108790, the pyc allele of *Corynebacterium glutamicum*, which allele is described in EP 1 108 790 and which codes for a protein with pyruvate carboxylase activity in which L-proline at position 458 of the amino acid sequence is substituted by L-serine, the pyc alleles of *Corynebacterium glutamicum*, which alleles are described in WO 02/31158 and in particular EP1325135B1 and which code for proteins with pyruvate carboxylase activity which feature one or more of the amino acid substitutions selected from the group consisting of L-valine at position 1 substituted by L-methionine, L-glutamic acid at position 153 substituted by L-aspartic acid, L-alanine at position 182 substituted by L-serine, L-alanine at position 206 substituted by L-serine, L-histidine at position 227 substituted by L-arginine, L-alanine at position 455 substituted by glycine and L-aspartic acid at position 1120 substituted by L-glutamic acid a lysC gene which codes for an aspartate kinase (LysC, EC No. 2.7.2.4), such as, for example, the lysC gene of the wild type of *Corynebacterium glutamicum*, which gene is described as SEQ ID NO:281 in EP-A-1108790 (see also accession number AX120085 and 120365) and the one described as SEQ ID NO:25 in WO 01/00843 (see accession number AX063743), a lysC$^{FBR}$ allele which codes for a feedback-resistant aspartate kinase variant, in particular according to Table 1, a lysE gene which codes for a lysine export protein (LysE), such as, for example, the lysE gene of the wild type *Corynebacterium glutamicum*, which gene is described in DE-A-195 48 222, the aat gene which codes for an aspartate aminotransferase (Aat, EC No. 2.6.1.1) (the aat gene of *Corynebacterium glutamicum* ATCC13032 is described for example in Kalinowski et al (*Journal of Biotechnology* 104:(1-3), 5-25 (2003); see also accession number NC_006958). It is referred to as aspB gene in that publication. In U.S. Pat. No. 6,004,773, a gene which codes for an aspartate aminotransferase is referred to as aspC. Marienhagen et al (*Journal of Bacteriology* 187 (22):7693-7646 (2005) refer to the aat gene as aspT gene.)), the zwa1 gene of the wild type of *Corynebacterium glutamicum*, which gene codes for the Zwa1 protein (U.S. Pat. No. 6,632,644).

In general, overexpression is understood as meaning an increase in the intracellular concentration or activity of a ribonucleic acid, of a protein or of an enzyme. The above-mentioned increase in the concentration or activity of a gene product can be achieved for example by increasing the copy number of the corresponding polynucleotides by at least one copy.

A widely used method of increasing the copy number consists in incorporating the corresponding gene or allele into a vector, preferably into a plasmid, which is replicated by a coryneform bacterium. Examples of suitable plasmid vectors are pZl (Merkel et al., *Applied and Environmental Microbiology* 64:549-554 (1989)) or the pSELF vectors described by Tauch et al. (*Journal of Biotechnology* 99:79-91 (2002)). A review on the subject of plasmids in *Corynebacterium glutamicum* is found in Tauch et al. (*Journal of Biotechnology* 104:27-40 (2003)).

Another widely used method of achieving overexpression is the chromosomal gene amplification method. In this method, at least one additional copy of the gene or allele of interest is introduced into the chromosome of a coryneform bacterium.

In one embodiment as described for example in Reinscheid et al. (*Applied and Environmental Microbiology* 60:126-132 (1994)) for the hom-thrB operon, a plasmid which comprises the gene of interest and which does not replicate in *C. glutamicum* is transferred into a coryneform bacterium. After homologous recombination by means of a crossover event, the resulting strain comprises at least two copies of the gene, or allele, in question.

In another embodiment, which is described in WO 03/040373 and US-2003-0219881-A1, one or more copy/copies of the gene of interest is introduced into a desired chromosomal locus of *C. glutamicum* by means of at least two recombination events. In this manner, for example a copy of a lysC allele, which codes for an L-lysine insensitive aspartate kinase, is incorporated into the gluB gene of *C. glutamicum*.

In a further embodiment, which is described in WO 03/014330 and US-2004-0043458-A1, at least two recombination events at the natural locus are used to incorporate at least one further copy of the gene of interest, preferably in tandem arrangement relative to the existing gene or allele. In this manner, for example a tandem duplication of a lysC$^{FBR}$ allele was obtained at the natural lysC gene locus.

A further method of obtaining an overexpression consists in linking the corresponding gene, or allele, with a promoter, or an expression cassette, so that it is operably linked. Suitable promoters for *Corynebacterium glutamicum* are described for example in the review article by Patek et al. (*Journal of Biotechnology* 104(1-3):311-323 (2003). The dapA promoter variants described by Vasicova et al (*Journal of Bacteriology* 181:6188-6191 (1999)), for example the promoter A25, can be employed in the same manner. The gap promoter of *Corynebacterium glutamicum* (EP 06007373) can also be used. Finally, the promoters T3, T7, SP6, M13, lac, tac and trc described by Amann et al. (*Gene* 69(2):301-315 (1988)) and Amann and Brosius (*Gene* 40(2-3):183-190 (1985)), which are well known, may be used. Such a promoter can be introduced for example upstream of the gene in question, typically at a distance of approximately 1-500 nucleotides from the start codon, of a recombinant coryneform bacterium. It is furthermore possible to link an isolated polynucleotide which codes for a corresponding protein with a promoter and to incorporate the expression unit obtained into an extrachromosomally replicating plasmid or into the chromosome of a coryneform bacterium.

Moreover, it is possible to mutate the promoter and regulatory region or the ribosomal binding site which is located upstream of the structural gene. Thus, it is possible to use the mutated promoter region according to the invention according to SEQ ID NO:9 or SEQ ID NO:13 for overexpression purposes.

Expression is also improved by measures for extending the life of the mRNA. Moreover, preventing the degradation of the enzyme protein also enhances the enzymatic activity. As an alternative, it is furthermore possible to obtain the overexpression of the gene or allele in question by modifying the media composition and the culture conditions.

The overexpression measures result in increasing the activity or concentration of the protein in question by in general at least 10%, 25%, 50%, 75%, 100%, 150%, 200%, 300%, 400% or 500%, up to a maximum of 1000% or 2000%, based on the activity or concentration of the protein in the starting microorganism or parent strain. A starting microorganism or parent strain is understood as meaning a microorganism on which the measures of the invention are practised.

The concentration of the protein can be determined in the gel via 1- and 2-dimensional protein gel separation followed by visual identification of the protein concentration with a suitable analytical software. A customary method of preparing the protein gels in coryneform bacteria and for identifying the proteins is the procedure described by Hermann et al. (*Electrophoresis* 22:1712-23 (2001)). The protein concentration can also be determined by Western blot hybridization with an antibody which is specific for the protein to be detected (Sambrook, et al., Molecular cloning: a laboratory manual. $2^{nd}$ Ed. Cold Spring Harbor Laboratory Press, Cold Spring Harbor, N.Y., 1989) followed by visual evaluation with suitable software for the determination of concentrations (Lohaus and Meyer (1998) Biospektrum 5:32-39; Lottspeich, *Angewandte Chemie* 38: 2630-2647 (1999)).

For the production of L-lysine, it may furthermore be advantageous not only to use the promoter region according to the invention, but simultaneously, if appropriate with simultaneous overexpression of at least one of the genes selected from the abovementioned group of genes, to weaken or to knock out one or more of the endogenous genes selected from the group consisting of:

a pgi gene, which codes for glucose 6-phosphate isomerase (Pgi, EC No. 5.3.1.9), such as, for example, the pgi gene of *Corynebacterium glutamicum*, which gene is described in U.S. Pat. No. 6,586,214 and U.S. Pat. No. 6,465,238, an hom gene which codes for homoserine dehydrogenase (Hom, EC No. 1.1.1.3), such as, for example, the hom gene of *Corynebacterium glutamicum*, which gene is described in EP-A-0131171, a thrB gene which codes for homoserine kinase (ThrB, EC No. 2.7.1.39), such as, for example, the thrB gene of *Corynebacterium glutamicum*, which gene is described by Peoples et al. (*Molecular Microbiology* 2: 63-72) (1988)), and a pfkB gene which codes for phosphofructokinase (PfkB, EC No. 2.7.1.56), such as, for example, the pfkB gene of *Corynebacterium glutamicum*, which gene is described in WO 01/00844 (sequence No. 57), an mdh gene which codes for malate dehydrogenase (Mdh, EC No. 1.1.1.37), such as, for example, as described in WO 02/02778, an mqo gene which codes for malate-quinone oxidoreductase (Mqo, EC No. 1.1.99.16), such as, for example, as described in U.S. Pat. No. 7,094,106 and PCT/EP2005/057216.

In this context, the term "weakening" describes the reduction or knocking-out of the intracellular activity of one or more enzymes (proteins) in a microorganism which are encoded by the corresponding DNA, for example by using a weak promoter or by using a gene, or allele, which codes for a correspoding enzyme with a lower activity or which inactivates the corresponding gene or enzyme (protein), and, if appropriate, combining these measures.

As the result of the measures of the weakening, the activity or the concentration of the protein in question is generally lowered to from 0 to 75%, from 0 to 50%, from 0 to 25%, from 0 to 10% or from 0 to 5% of the activity or concentration of the wild-type protein, or of the activity or concentration of the protein in the starting microorganism.

Suitable mutations for generating a weakening are transitions, transversions, insertions and deletions of at least one (1) base pair or nucleotide. Depending on the effect on the enzyme activity, of the amino acid substitution caused by the mutation, the terms "missense mutations" or "nonsense mutations" are also used. The missense mutation leads to a substitution of a given amino acid in a protein by another, being in particular a nonconservative amino acid substitution. This adversely affects the functionality or activity of the protein and reduces it to a value of from 0 to 75%, from 0 to 50%, from 0 to 25%, from 0 to 10% or from 0 to 5%. The nonsense mutation leads to a stop codon in the coding region of the gene and thus to premature termination of the translation. Insertions or deletions of at least one base pair in a gene lead to "frame shift mutations", with the result that incorrect amino acids are incorporated or that the translation is prematurely terminated. If as the result of the mutation, a stop codon is generated in the coding region, this likewise leads to premature termination of the translation. The abovementioned measures are preferably carried out in the 5'-terminal part of the coding region, which codes for the N terminus of the polypeptide. If the total length of a polypeptide (measured as the number of chemically bonded L-lysines) is referred to as 100%, then the N terminus of the polypeptide includes—within the scope of the present invention—the part of the amino acid sequence which, calculated from the starting amino acid L-formylmethionine, comprises 80% of the subsequent L-lysines.

Further instructions on the generation of such mutations belong to the prior art and can be found in known textbooks of genetics and molecular biology such as, for example, the textbook by Knippers ("Molekulare Genetik" [Molecular Genetics], $6^{th}$ edition, Georg Thieme Verlag, Stuttgart, Germany, 1995), that of Winnacker ("Gene and Klone" [Genes and Clones], VCH Verlagsgesellschaft, Weinheim, Germany, 1990) or that of Hagemann ("Allgemeine Genetik" [General Genetics], Gustav Fischer Verlag, Stuttgart, 1986). Further measures are described in the prior art.

One method for the directed reduction of gene expression consists in placing the gene to be weakened under the control of a promoter which can be induced by the addition of specific amounts of IPTG (isopropyl-β-D-thiogalactopyranoside), such as, for example, the trc promoter or the tac promoter. Vectors which are suitable for this purpose are, for example, the *Escherichia coli* expression vector pXK99E (WO0226787; deposited in accordance with the Budapest Treaty on Jul. 31, 2001, in DH5alpha/pXK99E as DSM14440 at the Deutsche Sammlung für Mikroorganismen and Zellkulturen (DSMZ, Brunswick, Germany)) or pVWEx2 (Wendisch, Ph. D. thesis, Berichte des Forschungszentrums Jülich, Jü-3397, ISSN 0994-2952, Jülich, Germany (1997)), which make possible the IPTG-dependent expression of the cloned gene in *Corynebacterium glutamicum*.

This method was employed for example in patent specification WO0226787 for the regulated expression of the deaD gene by integrating the vector pXK99EdeaD into the genome of *Corynebacterium glutamicum* and by Simic et al. (*Applied and Environmental Microbiology* 68:3321-3327 (2002)) for the regulated expression of the glyA gene by integration of the vector pK18mobglyA' into *Corynebacterium glutamicum*.

A further method for the specific reduction of gene expression is the antisense technique, where short oligodeoxynucleotides or vectors are introduced into the target cells for the synthesis of longer antisense RNA. In these cells, the antisense RNA can bind to complementary sections of specific mRNAs and reduce their stability or block translatability. The skilled worker will find an example in this context in Srivastava et al. (*Applied Environmental Microbiology* 2000 October; 66 (10): 4366-4371).

The isolated coryneform bacteria which are obtained by the measures of the invention feature a secretion/excretion or production of the desired amino acid in a fermentation process which is increased over that of the starting strain or parent strain employed.

Isolated bacteria are understood as meaning the isolated, or generated, mutants and recombinant bacteria, in particular coryneform bacteria, according to the invention in which a promoter region comprising a substitution of thymine by guanine at position 36, a substitution of cytosine by guanine at position 37, a substitution of guanine by thymine at position 40 and a substitution of cytosine by adenine at position 42 is present.

They are preferably understood as being the isolated, or generated, mutants and recombinant bacteria, in particular coryneform bacteria, according to the invention which comprise a dapB allele which codes for a dihydrodipicolinate reductase, where at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) is present in the promoter region of the dapB allele.

The performance of the isolated bacteria or of the fermentation process using the same with regard to one or more of the parameters of the group consisting of product concentration (product per volume), product yield (product formed per consumed carbon source) and product formation (product formed per volume and time) or else other process parameters and combinations thereof is improved by at least 0.5%, at least 1%, at least 1.5% or at least 2% based on the starting strain or parent strain or the fermentation process using the same.

The isolated coryneform bacteria according to the invention can be grown continuously—such as, for example, as described in PCT/EP2004/008882—or batchwise by the batch method or the fed-batch method or the repeated fed-batch method for the purposes of producing L-amino acids. An overview of known cultivation methods can be found in the textbook by Chmiel (Bioprozesstechnik 1 Einführung in die Bioverfahrenstechnik (Gustav Fischer Verlag, Stuttgart, 1991)) or in the textbook by Storhas (Bioreaktoren and periphere Einrichtungen (Vieweg Verlag, Brunswick/Wiesbaden, 1994)).

The culture medium or fermentation medium to be used must satisfy the demands of the particular strains in a suitable manner. The textbook "Manual of Methods for General Bacteriology" of the American Society for Bacteriology (Washington D.C., USA, 1981) contains descriptions of culture media for various microorganisms. The terms culture medium, fermentation medium and nutrient medium, or medium, are interchangeable.

Carbon sources which can be employed are sugars and carbohydrates such as, for example, glucose, sucrose, lactose, fructose, maltose, molasses, sucrose-comprising solutions from beet sugar or cane sugar production, starch, starch hydrolysate and cellulose, oils and fats such as, for example, soya oil, sunflower oil, peanut oil and coconut fat, fatty acids such as, for example, palmitic acid, stearic acid and linoleic acid, alcohols such as, for example, glycerol, methanol and ethanol, and organic acids such as, for example, acetic acid. These substances can be used singly or as a mixture.

Nitrogen sources which can be used are organic nitrogen-containing compounds such as peptones, yeast extract, meat extract, malt extract, cornsteep liquor, soybean meal and urea, or inorganic compounds such as ammonium sulfate, ammonium chloride, ammonium phosphate, ammonium carbonate and ammonium nitrate. The nitrogen sources may be used singly or as a mixture.

Phosphorus sources which may be used are phosphoric acid, potassium dihydrogen phosphate or dipotassium hydrogen phosphate, or the corresponding sodium-containing salts.

The culture medium must furthermore comprise salts, for example in the form of chlorides or sulfates of metals such as, for example, sodium, potassium, magnesium, calcium and iron, such as, for example, magnesium sulfate or iron sulfate, which are required for growth. Finally, essential growth factors such as amino acids, for example homoserine, and vitamins, for example thiamine, biotin or pantothenic acid may be employed in addition to the abovementioned substances. Moreover, suitable precursors of the amino acid in question may be added to the culture medium.

The feedstock mentioned may be added to the culture in the form of a single batch or fed in a suitable manner during cultivation.

The pH of the culture is controlled in a suitable manner by employing basic compounds such as sodium hydroxide, potassium hydroxide, ammonia or ammonia water, or acidic compounds such as phosphoric acid or sulfuric acid. In general, the pH is adjusted to a value of from 6.0 to 8.5 preferably from 6.5 to 8.

Antifoam agents, such as, for example, fatty acid polyglycol esters may be employed to control foam development. To maintain plasmid stability, suitable selectively acting substances such as, for example, antibiotics may be added to the medium. To maintain aerobic conditions, oxygen or oxygen-containing gas mixtures, for example air, are passed into the culture. The use of liquids enriched with hydrogen peroxide is also possible.

If appropriate, the fermentation is conducted at superatmospheric pressure, for example at a superatmospheric pressure of from 0.03 to 0.2 MPa. The culture temperature is normally 25° C. to 40° C. and preferably 30° C. to 37° C. In the case of a batch process, the cultivation is continued until a maximum of the desired amino acid has formed. This aim is normally achieved within 10 hours to 160 hours. Longer culture periods are possible in the case of continuous processes.

Suitable fermentation media are described, inter alia, in U.S. Pat. No. 6,221,636, U.S. Pat. No. 5,840,551, U.S. Pat. No. 5,770,409, U.S. Pat. No. 5,605,818, U.S. Pat. No. 5,275,940, U.S. Pat. No. 4,275,157 and U.S. Pat. No. 4,224,409.

Methods for the determination of L-lysine are known from the prior art. For example, the analysis can be carried out as described by Spackman et al. (*Analytical Chemistry*, 30:1190 (1958)) by anion exchange chromatography followed by ninhydrin derivatization, or it can be carried out by reversed phase HPLC as described by Lindroth et al. (*Analytical Chemistry* 51:1167-1174 (1979)).

Accordingly, the invention relates to a process for the production of L-lysine in which:
 a) an isolated coryneform bacterium is fermented in a suitable medium, where the bacterium contains a promoter region comprising a substitution of thymine by guanine at position 36, a substitution of cytosine by guanine at position 37, a substitution of guanine by thymine at position 40 and a substitution of cytosine by adenine at position 42, and
 b) the L-lysine accumulates in the fermentation liquor or in the cells of the isolated coryneform bacterium.

Accordingly, the invention preferably relates to a process for the production of L-lysine in which:
 a) an isolated coryneform bacterium is fermented in a suitable medium, where the bacterium comprises a dapB allele which codes for a polypeptide with dihydrodipicolinate reductase enzyme activity, where at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) is present in the promoter region of the dapB allele, and
 b) the L-lysine accumulates in the fermentation liquor or in the cells of the isolated coryneform bacterium.

In general, this is followed by collecting the L-lysine accumulated in the nutrient medium or in the fermentation liquor and/or in the bacterial cells in order to obtain a solid or liquid product.

A fermentation liquor is understood as meaning a fermentation medium in which a microorganism has been cultured for a certain period of time and at a certain temperature. The fermentation medium, or the medium employed during the fermentation, comprises/comprise all substances or components which ensure the multiplication of the microorganism and the formation of the desired amino acid.

When the fermentation is complete, the fermentation liquor formed will, correspondingly, comprise a) the biomass (cell matter) of the microorganism formed as the result of the multiplication of the microorganism cells, b) the desired amino acid formed in the course of the fermentation, c) the organic by-products formed in the course of the fermentation, and d) the components of the fermentation medium/fermentation media employed, or the feedstock such as, for example, vitamins such as biotin, amino acids such as homoserine or salts such as magnesium sulfate, which have not been consumed by the fermentation.

The organic by-products include substances which are generated, and, if appropriate, excreted/secreted by the microorganisms employed in the fermentation, if appropriate in addition to the respective desired L-amino acid. These include L-amino acids which, in comparison with the desired amino acid, account for less than 30%, 20% or 10%. They furthermore include organic acids which have attached to them one to three carboxyl groups, such as, for example, acetic acid, lactic acid, citric acid, malic acid or fumaric acid. Finally, they also include sugars such as, for example, trehalose.

Typical fermentation liquors which are suitable for industrial purposes will typically have an amino acid content of from 30 g/kg to 200 g/kg or from 40 g/kg to 175 g/kg or from 50 g/kg to 150 g/kg. The biomass content (as dried biomass) will generally amount to 20 to 50 g/kg.

In the case of the amino acid L-lysine, essentially four different product forms are known in the prior art. One group of L-lysine-containing products comprises concentrated, aqueous, alkaline solutions of purified L-lysine (EP-B-0534865). A further group such as, for example, described in U.S. Pat. No. 6,340,486 and U.S. Pat. No. 6,465,025 comprises aqueous, acidic, biomass-containing concentrates of L-lysine-containing fermentation liquors. The best-known group of solid products comprises pulverulent or crystalline forms of purified or pure L-lysine which is typically present in the form of a salt such as, for example, L-lysine monohydrochloride. A further group of solid product forms is described for example in EP-B-0533039. The product form described therein comprises, besides L-lysine, most of the feedstocks which have been used during the fermentative production, but not consumed, and, if appropriate, the biomass of the microorganism employed with a content of >0%-100%.

According to the various product forms, a very wide range of processes are known in which the L-amino acid is collected, isolated or purified from the fermentation liquor in order to produce the L-amino acid-containing product or the purified L-amino acid.

Methods which are used for the preparation of solid, pure L-amino acids are essentially methods of ion-exchange chromatography, if appropriate using active charcoal, and crystallization methods. In the case of lysine, this gives the corresponding base or a corresponding salt such as, for example, the monohydrochloride (Lys-HCl) or lysine sulfate ($Lys_2$-$H_2SO_4$).

In the case of lysine, EP-B-0534865 describes a process for the production of aqueous, basic L-lysine-containing solutions from fermentation liquors. In the method described therein, the biomass is removed from the fermentation liquor and discarded. A pH of between 9 and 11 is set by means of a base such as, for example, sodium hydroxide, potassium hydroxide or ammonium hydroxide. After concentration and cooling, the mineral constituents (inorganic salts) are separated from the liquor by crystallization and either used as fertilizer or discarded.

In the case of processes for producing lysine, using the bacteria according to the invention, processes which generate products which comprise constituents of the fermentation liquor are also employed. These are used in particular as animal feed additives.

Depending on requirements, all or some of the biomass can be removed from the fermentation liquor by separation methods, for example centrifugation, filtration, decanting or a combination of these, or left completely in it. If appropriate, the biomass or the biomass-containing fermentation liquor is inactivated during a suitable process step, for example by thermal treatment (heating) or by adding acid.

The chemical constituents of the biomass are, inter alia, the cell envelope, for example the peptidoglycan and the arabinogalactan, the protein or polypeptide, for example the dihydrodipicolinate reductase polypeptide, lipids and phospholipids and nucleic acids (DNA and RNA), for example polynucleotides comprising the mutation according to the invention. As the consequence of the measures of the inactivation and/or of the further process steps (for example acidification, spray drying, granulation and the like), nucleic acids are typically present in the form of fragments with a length of, inter alia, ≥40-60 bp, >60-80 bp, >80-100 bp, >100-200 bp, >200-300 bp, >300-400 bp, >400-500 bp, >500-750 bp, >750-1000 bp, >1000-1250 bp, >1250-1500 bp, >1500-1750 bp, >1750-2000 bp, >2000-2500 bp, >2500-3000 bp, >3000-4000 bp, >4000-5000 bp.

In one procedure, the biomass is removed completely or almost completely so that no (0%) or not more than 30%, not more than 20%, not more than 10%, not more than 5%, not more than 1% or not more than 0.1% of biomass remains in the product produced. In another procedure, the biomass is not removed, or is removed only in small proportions, so that all (100%) or more than 70%, 80%, 90%, 95%, 99% or 99.9% of biomass remains in the product produced. In one process according to the invention, accordingly, the biomass is removed in proportions of ≥0% to ≤100%.

Finally, the fermentation liquor obtained after the fermentation can be adjusted, before or after the complete or partial removal of the biomass, to an acidic pH with an inorganic acid such as, for example, hydrochloric acid, sulfuric acid or phosphoric acid, or organic acids such as, for example, propionic acid (GB 1,439,728 or EP 1 331 220). Equally, it is possible to acidify the fermentation liquor with the complete biomass content (U.S. Pat. No. 6,340,486 or U.S. Pat. No. 6,465,025). Finally, the liquor can also be stabilized by adding sodium bisulfite ($NaHSO_3$, GB 1,439,728) or another salt, for example ammonium salt, alkali metal salt or alkaline earth metal salt of the sulfurous acid.

If appropriate, organic or inorganic solids present in the fermentation liquor are removed partially or completely during the removal of the biomass. The organic by-products dissolved in the fermentation liquor and the dissolved unconsumed components of the fermentation medium (feedstocks) remain at least partly (>0%), preferably to the extent of at least 25%, especially preferably to the extent of at least 50% and very especially preferably to the extent of at least 75% in the product. If appropriate, they also remain completely (100%) or almost completely, meaning >95% or >98%, in the product. In this sense, the term "based on fermentation liquor" means that a product comprises at least part of the components of the fermentation liquor.

Subsequently, water is removed from the liquor, or the liquor is thickened or concentrated, using known methods such as, for example, with the aid of a rotary evaporator, thin-film evaporator, falling-film evaporator, by reverse osmosis or by nanofiltration. This concentrated fermentation liquor can then be worked up by methods of freeze-drying, spray-drying, spray granulation or by other processes as described for example in the circulating fluidized bed according to PCT/EP2004/006655 to give free-flowing products, in particular to give a finely particulate powder or preferably coarse granules. If appropriate, a desired product is isolated from the resulting granules by screening or dust removal.

It is likewise possible to dry the fermentation liquor directly, i.e. without previous concentration by spray drying or spray granulation.

"Free-flowing" means powders which flow unimpeded out of a series of glass orifice vessels with orifices of different sizes, at least out of the vessel with the 5 mm (millimeter) orifice (Klein: Seifen, Öle, Fette, Wachse 94, 12 (1968)).

"Finely particulate" is understood as meaning a powder with a predominating (>50%) proportion of a particle size of diameter 20 to 200 µm.

"Coarse" is understood as meaning a product with a predominating (>50%) proportion of a particle size of diameter 200 to 2000 µm.

The particle size determination can be carried out by methods of laser diffraction spectrometry. Corresponding methods are described in the textbook "Teilchengrößenmessung in der Laborpraxis" by R. H. Müller and R. Schuhmann, Wissenschaftliche Verlagsgesellschaft Stuttgart (1996) or in the textbook "Introduction to Particle Technology" by M. Rhodes, published by Wiley & Sons (1998).

The free-flowing, finely particulate powder can in turn be converted into a coarse, very free-flowing, storable and substantially dust-free product by means of suitable compaction or granulation processes.

The term "dust-free" means that the product comprises only a small proportion (<5%) of particle sizes below 100 µm in diameter.

For the purposes of the present invention, "storable" means a product which can be stored for at least one (1) year or longer, preferably at least 1.5 years or longer, especially preferably two (2) years or longer in a dry and cool environment without any substantial loss (<5%) of the respective amino acid occurring.

Accordingly, the invention furthermore relates to a process for the production of an L-amino acid, preferably L-lysine, -containing product, preferably animal feed additive, from fermentation liquors, characterized by the steps a) culturing and fermentation, in a fermentation medium, of an L-lysine-excreting/secreting coryneform bacterium, where, in the bacterium, a promoter region according to the invention comprising a substitution of thymine by guanine at position 36, a substitution of cytosine by guanine at position 37, a substitution of guanine by thymine at position 40 and a substitution of cytosine by adenine at position 42 is present, b) removal of the biomass formed during the fermentation in an amount of from 0 to 100% by weight, and c) drying the fermentation liquor obtained in a) and/or b) in order to obtain the product in the desired form of a powder or granules, where, if appropriate, an acid selected from the group consisting of sulfuric acid, phosphoric acid or hydrochloric acid is added before step b) or c). Step a) or b) is preferably followed by removal of water from the L-lysine-containing fermentation liquor (concentration).

The invention furthermore preferably relates to a process for the production of an L-amino acid, preferably L-lysine, -containing product, preferably animal feed additive, from fermentation liquors, characterized by the steps a) culturing and fermentation, in a fermentation medium, of an L-lysine-secreting/excreting coryneform bacterium, which comprises at least one dapB allele which codes for a polypeptide with dihydrodipicolinate reductase activity, where at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) is present in the promoter region of the dapB allele, b) removal of the biomass formed during the fermentation in an amount of from 0 to 100% by weight, and c) drying the fermentation liquor obtained in a) and/or b) in order to obtain the product in the desired form of a powder or granules, where, if appropriate, an acid selected from the group consisting of sulfuric acid, phosphoric acid or hydrochloric acid is added before step b) or c). Step a) or b) is preferably followed by removal of water from the L-lysine-containing fermentation liquor (concentration).

The invention furthermore relates to a process for the production of a lysine-sulfate-containing product which is described in principle in DE 102006016158 and in which the fermentation liquor obtained using the microorganisms according to the invention from which, if appropriate, all or some of the biomass has been removed, is further processed by carrying out a method comprising at least the following steps:

a) the pH is reduced by adding sulfuric acid to 4.0 to 5.2, in particular 4.9 to 5.1, and a molar sulfate/L-lysine ratio of from 0.85 to 1.2, preferably 0.9 to 1.0, especially preferably >0.9 to <0.95, is adjusted in the liquor, if appropriate by adding one further or more sulfate-containing compound(s), and b) the mixture thus obtained is concentrated by removal of water and, if appropriate, granulated, where, if appropriate, one or two of the following measures is/are carried out before step a):

c) measurement of the molar sulfate/L-lysine ratio to ascertain the required amount of sulfate-containing compound(s)

d) addition of a sulfate-containing compound selected from the group consisting of ammonium sulfate, ammonium hydrogen sulfate and sulfuric acid in suitable ratios.

If appropriate, a salt of sulfurous acid, preferably alkali metal hydrogen sulfate, especially preferably sodium hydrogen sulfate, is furthermore added before step b) in a concentration of from 0.01 to 0.5% by weight, preferably 0.1 to 0.3% by weight, especially preferably 0.1 to 0.2% by weight, based on the fermentation liquor.

Preferred sulfate-containing compounds for the purposes of the abovementioned process steps which should be mentioned are, in particular, ammonium sulfate and/or ammonium hydrogen sulfate or suitable mixtures of ammonia and sulfuric acid, and sulfuric acid itself.

The molar sulfate/L-lysine ratio V is calculated by the formula: $V=2\times[SO_4^{2-}]/[L\text{-lysine}]$. This formula takes account of the fact that the $SO_4^{2-}$ anion has two charges. A ratio of $V=1$ means that a stoichiometric composition of $Lys_2(SO_4)$ is present, whereas a ratio of $V=0.9$ results in a 10% sulfate deficit and a ratio of $V=1.1$ a 10% sulfate excess.

It is advantageous to employ, during the granulation or compaction, the usual organic or inorganic auxiliaries or carriers such as starch, gelatin, cellulose derivatives or similar substances, as are normally used in the processing of food products or feeds as binders, gelling agents or thickeners, or further substances such as, for example, silicas, silicates (EP0743016A) or stearates.

It is furthermore advantageous to provide the surface of the resulting granules with oils as described in WO 04/054381. Oils which can be used are mineral oils, vegetable oils or mixtures of vegetable oils. Examples of such oils are soya oil, olive oil, soya oil/lecithin mixtures. Silicone oils, polyethylene glycols or hydroxyethylcelluloses are equally also suitable. By treating the surfaces with said oils, an increased abrasion resistance of the product and a reduction in the dust content are achieved. The oil content in the product amounts to from 0.02 to 2.0% by weight, preferably 0.02 to 1.0% by weight and very especially preferably 0.2 to 1.0% by weight based on the total amount of the feed additive.

Preferred products have a proportion of ≥97% by weight of a particle size of from 100 to 1800 μm or a proportion of ≥95% by weight of a particle size of from 300 to 1800 μm in diameter. The proportion of dust, i.e. particles with a particle size <100 μm is preferably >0 to 1% by weight, especially preferably not more than 0.5% by weight.

Alternatively, however, the product may also be absorbed onto an organic or inorganic carrier which is known and customary in the processing of feeds, such as, for example, silicas, silicates, meals, brans, flours, starches, sugars or others, and/or be mixed and stabilized with customary thickeners or binders. Use examples and processes in this context are described in the literature (Die Mühle+Mischfuttertechnik 132 (1995) 49, page 817).

Finally, the product can also be brought into a state in which it is stable to digestion by animal stomachs, in particular the stomach of ruminants, by means of coating processes using film formers such as, for example, metal carbonates, silicas, silicates, alginates, stearates, starches, gums and cellulose ethers as described in DE-C-4100920.

To adjust a desired amino acid concentration in the product, it is possible, depending on requirements, to add the appropriate amino acid during the process in the form of a concentrate or, if appropriate, of a substantially pure substance or its salt in liquid or solid form. These can be added singly or as mixtures to the resulting or concentrated fermentation liquor, or else during the drying or granulation process.

The invention furthermore relates to a process for the production of a solid lysine-containing product as described in principle in US 20050220933 and which includes the work-up of the fermentation liquor obtained using the microorganisms according to the invention in the following steps:

a) filtration of the fermentation liquor, preferably using a membrane filter, so that a biomass-containing sludge and a filtrate are obtained, b) concentrating the filtrate, preferably such that a solids content of from 48 to 52% by weight is obtained, c) granulation of the concentrate obtained in step b), preferably at a temperature of from 50° C. to 62° C., and d) coating of the granules obtained in c) with one or more of the coating agent(s).

To carry out the coating in step d), it is preferred to use coating agents selected from the group consisting of d1) the biomass obtained in step a), d2) an L-lysine-containing compound, preferably selected from the group consisting of L-lysine hydrochloride or L-lysine sulfate, d3) a substantially L-lysine-free substance with an L-lysine content of <1% by weight, preferably <0.5% by weight, preferably selected from the group consisting of starch, carrageenan, agar, silicas, silicates, meals, brans and flours, and d4) a water-repellent substance, preferably selected from the group consisting of oils, polyethylene glycols and liquid paraffins.

In the case of lysine, the ratio of the ions during the production of lysine-containing products is preferably adjusted so that the equivalent ion ratio corresponding to the following formula: $2\times[SO_4^{2-}]+[Cl^-]-[NH_4^+]-[Na^+]-[K^+]-2\times[Mg^{2+}]-2\times[Ca^{2+}]/[L\text{-Lys}]$ results in 0.68 to 0.95, preferably 0.68 to 0.90, as described by Kushiki et al. in US 20030152633 (the molar concentrations are to be indicated within the "[ ]").

In the case of lysine, the solid product produced in this manner has, based on the fermentation liquor, a lysine content (as lysine base) of 10% by weight to 70% by weight or 20% by weight to 70% by weight, preferably 30% by weight to 70% by weight and very especially preferably 40% by weight to 70% by weight, based on the dry matter of the product. Maximum contents of lysine base of 71% by weight, 72% by weight, 73% by weight are also possible.

The water content of the solid product amounts to up to 5% by weight, preferably up to 4% by weight, and especially preferably less than 3% by weight.

The invention therefore also relates to an L-lysine-containing feed additive based on a fermentation liquor, which shows the following features:

a) a lysine content (as base) of at least 10% by weight to not more than 73% by weight, b) a water content of 5% by weight at the most, and c) a biomass content corresponding to at least 0.1% of the biomass present in the fermentation liquor, where the biomass, which, if appropriate, is inactivated is formed by coryneform bacteria according to the invention.

The mutant *Corynebacterium glutamicum* DM1729_mut#3.2e according to the invention which has at position −49 a substitution of cytosine by adenine (C (−49) A mutation), at position −51 a substitution of guanine by thymine (G (−51) T mutation), at position −54 a substitution of cytosine by guanine (C (−54) G mutation) and at position −55 a substitution of thymine by guanine (T (−55) G mutation) in the promoter region of the dapB allele, has been deposited on Mar. 12, 2008 at the Deutsche Sammlung für Mikroorganismen and Zellkulturen (DSMZ, Brunswick, Germany) as DSM 22076.

In what follows, the present invention is illustrated in greater detail with reference to use examples.

EXAMPLES

Example 1

Mutagenesis of the L-Lysine-Producing Strain DM1729

*Corynebacterium glutamicum* strain DM1729 was employed as the starting strain for mutagenesis with N-methyl-N'-nitro-N-nitrosoguanidine (MNNG). Strain DM1729 is an aminoethylcysteine-resistant mutant (pycP458S, homV59A, lysCT311I) of *Corynebacterium glutamicum* ATCC13032 (Georgi et al., Metabolic Engineering 7:291-301, 2005) and has been deposited on 16 Sep. 2005 at the Deutsche Sammlung far Mikroorganismen and Zellkulturen (DSMZ, Brunswick, Germany) under the name DSM17576.

Strain DM1729 was cultured in 10 ml of LB broth (Merck, Darmstadt, Germany), in a 100 ml Erlenmeyer flask for 24 hours at 33° C. and 200 rpm on a rotary shaker type Certomat BS-1 (B. Braun Biotech International, Melsungen, Germany). Thereafter, the culture was spun down, the sediment was resuspended in 10 ml of 0.9% strength NaCl solution, the suspension obtained was again spun down, and the sediment obtained was taken up in 10 ml 0.9% NaCl solution. 5 ml of this cell suspension were treated with 400 µg/ml MNNG for 15 minutes at 30° C. and 200 rpm on a shaker (see above). Thereafter, the mutagenesis batch was spun down and the sediment was taken up in 10 ml of 2% strength sodium thiosulfate in 0.9% strength NaCl buffer (pH=6.0). Thereafter, the cell suspension was diluted with 0.9% strength NaCl solution in the ratio 1:1000, 1:10000 and 1:100000, and aliquots were plated on brain-heart agar (Merck, Darmstadt, Germany). Approximately 4000 mutants were isolated in this manner.

Example 2

Performance Test of the Mutants of Strain DM1729

The mutants obtained in Example 1 were grown in a nutrient medium which is suitable for the production of lysine, and the lysine content in the culture supernatant was determined.

To this end, the clones were first multiplied on brain-heart agar plates (Merck, Darmstadt, Germany) for 24 hours at 33° C. Starting from these agar plate cultures, in each case one preculture was inoculated (10 ml of medium in 100 ml Erlenmeyer flask). The preculture medium used was the MM medium. The preculture was incubated on a shaker for 24 hours at 33° C. and 240 rpm. This preculture was used to inoculate a main culture so that the initial OD (660 nm) of the main culture was 0.1 OD. The MM medium was also used for the main culture.

Medium MM
CSL 5 g/l
MOPS 20 g/l
Glucose (autoclaved separately) 50 g/l
Salts:
$(NH_4)_2SO_4$) 25 g/l
$KH_2PO_4$ 0.1 g/l
$MgSO_4 * 7 H_2O$ 1.0 g/l
$CaCl_2 * 2 H_2O$ 10 mg/l
$FeSO_4 * 7 H_2O$ 10 mg/l
$MnSO_4 * H_2O$ 5.0 mg/l
Biotin (filter-sterilized) 0.3 mg/l
Thiamine*HCl (filter-sterilized) 0.2 mg/l
$CaCO_3$ 25 g/l CSL (Corn Steep Liquor), MOPS (morpholinopropanesulfonic acid) and the salt solution were brought to pH 7 with ammonia water and autoclaved. Thereafter, the sterile substrate and vitamin solutions and the $CaCO_3$, which had been autoclaved dry, were added.

The cultures were grown in volumes of 10 ml in 100 ml Erlenmeyer flasks provided with baffles. The temperature was 33° C., the speed 250 rpm and the atmospheric humidity 80%. After 24 hours, the optical density (OD) was determined at a measuring wavelength of 660 nm using a Biomek 1000 (Beckmann Instruments GmbH, Munich, Germany). The amount of lysine formed was determined using an amino acid analyzer from Eppendorf-BioTronik (Hamburg, Germany) by means of ion-exchange chromatography and post-column derivatization with ninhydrin detection. One mutant which was distinguished by an increased lysine formation was named DM1729_mut#3.2e.

TABLE 1

| Strain | OD(660) | Lysine-HCl (g/l) |
|---|---|---|
| DM1729 | 15.4 | 7.5 |
| DM1729_mut#3.2e | 15.3 | 8.4 |

Example 3

Sequencing of the dapB Allele of the Mutant DM1729_Mut#3.2e

Chromosomal DNA was isolated from clone DM1729_mut#3.2e using the method of Eikmanns et al. (Microbiology 140: 1817-1828 (1994)). A DNA segment which carries the dapB gene, or allele, was amplified with the aid of the polymerase chain reaction. On the basis of the sequence of the dapB gene which is known for *C. glutamicum* (Accession No. NC_006958: 2051238-2051984 (complementary)) and the upstream and downstream regions, the following primer oligonucleotides were selected for the PCR:

PdapBN1_1.p (SEQ ID NO:7): 5' CC GAATTCTGTAGTTGACGGCGTTCC 3'
PdapBN1_4.p (SEQ ID NO:8): 5' CC AAGCTTCCACCCGCTGCTGAAATG 3'

The primers shown were synthesized by MWG Biotech (Ebersberg, Germany), and the PCR reaction was carried out by the standard PCR method of Innis et al. (PCR Protocols. A Guide to Methods and Applications, 1990, Academic Press). The primers allow the amplification of an approximately 1.69 kb DNA segment which carries the dapB gene, or allele. Furthermore, the primers comprise the sequence for a cleavage site of the restriction endonuclease EcoRI or HindIII, which is identified in the above-shown nucleotide sequence by underlining.

The amplified DNA fragment which has a length of approximately 1.69 kb and which carries the dapB allele of strain DM1729_mut#3.2e was identified in a 0.8% agarose gel by electrophoresis, isolated from the gel and purified by the customary methods (QIAquick Gel Extraction Kit, Qiagen, Hilden).

The nucleotide sequence of the amplified DNA fragment or PCR product was determined by Agowa (Berlin, Germany) by sequencing. The sequence of the PCR product is shown in SEQ ID NO:5. The sequence of the coding region is additionally shown in SEQ ID NO: 1. The amino acid sequence, of the corresponding dihydrodipicolinate reductase protein, deduced with the aid of the program Patentin is shown in SEQ ID NO:2 and 6.

Position −49 (49 nucleotides upstream of the first nucleotide of the start codon) of the nucleotide sequence of the promoter region of the dapB allele of strain DM1729_mut#3.2e is occupied by the base adenine (a) (SEQ ID NO:5). The corresponding position of the wild-type gene is occupied by the base cytosine (SEQ ID NO:3).

Position −51 (51 nucleotides upstream of the first nucleotide of the start codon) of the nucleotide sequence of the promoter region of the dapB allele of strain DM1729_mut#3.2e is occupied by the base thymine (t) (SEQ ID NO:5). The corresponding position of the wild-type gene is occupied by the base guanine (SEQ ID NO:3).

Position −54 (54 nucleotides upstream of the first nucleotide of the start codon) of the nucleotide sequence of the promoter region of the dapB allele of strain DM1729_mut#3.2e is occupied by the base guanine (g) (SEQ ID NO:5). The corresponding position of the wild-type gene is occupied by the base cytosine (SEQ ID NO:3).

Position −55 (55 nucleotides upstream of the first nucleotide of the start codon) of the nucleotide sequence of the promoter region of the dapB allele of strain DM1729_mut#3.2e is occupied by the base guanine (g) (SEQ ID NO:5). The corresponding position of the wild-type gene is occupied by the base thymine (SEQ ID NO: 3).

The coding region of the dapB allele of strain DM1729_mut#3.2e shows no mutations.

The dapB allele, which comprises the bases −49a, −51t, −54g and −55g in the promoter region, is hereinbelow referred to as dapBN1 allele. The promoter region is referred to as PdapBN1.

The *Corynebacterium glutamicum* mutant DM1729_mut#3.2e, which comprises the bases −49a, −51t, −54g and −55g in the promoter region of the dapB allele, was deposited on Mar. 12, 2008 at the Deutsche Sammlung für Mikroorganismen and Zellkulturen (DSMZ, Brunswick, Germany) as DSM 22076.

Example 4

Substitution of the dapB Wild-Type Gene of Strain DM1729 by the dapBN1 Allele 4.1 Construction of the Substitution Vector pK18mobsacB_PdapBN1

The approximately 1.69 kb DNA fragment which has been described in Example 3, has been prepared by means of PCR and carries the PdapBN1 allele was incorporated into the chromosome of the *C. glutamicum* strain DM1729, which has been described in Example 1, by means of substitution mutagenesis with the aid of the sacB system described by Schafer et al. (Gene, 14, 69-73 (1994)). This system makes possible the generation, or selection, of allele substitutions which are the result of homologous recombination.

To this end, the approximately 1.69 kb PdapBN1 fragment was cleaved with the restriction endonucleases EcoRI and HindIII, identified in a 0.8% agarose gel by electrophoresis and finally isolated from the gel and purified by the customary methods (QIAquick Gel Extraction Kit, Qiagen, Hilden).

The mobilizable cloning vector pK18mobsacB was also digested with the restriction enzymes EcoRI and HindIII, and the ends were dephosphorylated with alkaline phosphatase (alkaline phosphatase, Boehringer Mannheim, Germany). The vector thus prepared was mixed with the approximately 1.69 kb PdapBN1 fragment, and the mixture was treated with T4 DNA ligase (Amersham-Pharmacia, Freiburg, Germany).

Thereafter, the *E. coli* strain S17-1 (Simon et al., *Bio/Technology* 1:784-791, 1993) was transformed with the ligation mixture (Hanahan, In. DNA Cloning. A Practical Approach. Vol. 1, ILR-Press, Cold Spring Harbor, N.Y., 1989). Selection of the plasmid-harboring cells was performed by plating the transformation mixture onto LB agar (Sambrook et al., Molecular Cloning: A Laboratory Manual. $2^{nd}$ Ed., Cold Spring Harbor, N.Y., 1989) which had been supplemented with 25 mg/l kanamycin.

Plasmid DNA was isolated from one transformant with the aid of the QIAprep Spin Miniprep Kit from Qiagen and verified by restriction cleavage with the enzyme EcoRI/HindIII or BanII/BspHI followed by agarosegel electrophoresis. The plasmid is named pK18mobsacB_PdapBN1 and is shown in FIG. 1.

4.2 Allele Exchange

The vector pK18mobsacB_PdapBN1 mentioned in Example 4.1 was transferred by conjugation into the *C. glutamicum* strain DM1729 using a protocol of Schäfer et al. (*Journal of Microbiology* 172:1663-1666 (1990)). The vector is not capable of autonomous replication in DM1729 and is only retained in the cell when it is present in chromosome-integrated form as the result of a recombination event. The selection of transconjugants, i.e. of clones with integrated pK18mobsacB_PdapBN1, was carried out by plating the conjugation mixture onto LB agar (Sambrook et al., Molecular Cloning: A Laboratory Manual. $2^{nd}$ Ed. Cold Spring Harbor, N.Y., 1989) which was supplemented with 15 mg/l kanamycin and 50 mg/l nalidixic acid. Kanamycin-resistant transconjugants were plated onto LB agar plates with 25 mg/l kanamycin and incubated for 24 hours at 33° C. To select mutants in which the excision of the plasmid had taken place as the consequence of a second recombination event, the clones were cultured unselectively in LB liquid medium for 30 hours, subsequently plated onto LB agar with 10% sucrose and incubated for 16 hours.

Like the starting plasmid pK18mobsacB, the plasmid pK18mobsacB_PdapBN1 comprises, besides the kanamycin resistance gene, a copy of the sacB gene which codes for the levan sucrase from *Bacillus subtilis*. The sucrose-inducible expression results in the formation of levan sucrase, which catalyzes the synthesis of the product levan, which is toxic to *C. glutamicum*. This is why only those clones in which the integrated pK18mobsacB_PdapBN1 has excized as the consequence of a second recombination event will grow in LB agar with sucrose. Depending on the position of the second recombination event with regard to the mutation site, the allele exchange, or incorporation of the mutation, takes place upon excision, or else the original copy remains in the host chromosome.

Approximately 40 to 50 colonies were examined for the phenotype "growth in the presence of sucrose" and "non-growth in the presence of kanamycin." In 4 colonies which exhibited the phenotype "growth in the presence of sucrose" and "non-growth in the presence of kanamycin", a region of the dapB allele, which region spanned the promoter mutation, was sequenced starting from the sequencing primer da1-2 (corresponds to the nucleotide sequence position 802-821 of the sequence from SEQ ID NO:3, which sequence is located upstream of the CDS of the dapB gene), by Agowa (Berlin, Germany) to prove that the mutation of the PdapBN1 allele is present in the chromosome. To this end, the da1-2 primer used was synthesized by Agowa: da1-2: 5' GGTGAAGGGC AACTTAAGTC 3' (SEQ ID NO:19).

In this manner, a clone which comprises the bases −49a, −51t, −54g and −55g in the promoter region of the dapB allele, and thus carries the PdapBN1 allele, was identified. This clone was referred to as strain DM1729_PdapBN1.

Example 5

Comparison of the Performance of Strain DM1729_PdapBN1 with that of the Starting Strain DM1729

The performance test of the *C. glutamicum* strain DM1729_PdapBN1 which was obtained in Example 5 was carried out as described in Example 2. The result of the test is shown in Table 2.

TABLE 2

| Strain | OD (660 nm) | Lysine-HCl g/l |
|---|---|---|
| DM1729 | 15.8 | 7.5 |
| DM1729_PdapBN1 | 15.7 | 8.3 |

---

What is claimed is:

1. An isolated mutant coryneform bacterium comprising a DNA fragment with promoter activity operably linked to a polynucleotide coding for a protein with dihydrodipicolinate reductase activity, wherein said DNA fragment comprises the sequence of SEQ ID NO:12 but with one or more substitutions selected from the group consisting of:
   a) substitution of the nucleobase thymine at position 36 of SEQ ID NO:12 by guanine;
   b) substitution of the nucleobase cytosine at position 37 of SEQ ID NO:12 by guanine;
   c) substitution of the nucleobase guanine at position 40 of SEQ ID NO:12 by thymine;
   d) substitution of the nucleobase cytosine at position 42 of SEQ ID NO:12 by adenine;
   and wherein:
   i) relative to a bacterial parent strain which does not carry said DNA fragment operably linked to a polynucleotide coding for a protein with dihydrodipicolinate reductase activity, said mutant coryneform bacterium produces more L-lysine when fermented in nutrient medium and under conditions suitable for lysine production; and
   ii) relative to a DNA fragment of SEQ ID NO:12 without any of said substitutions, said DNA fragment with the sequence of SEQ ID NO:12 with one or more of said substitutions has increased transcriptional activity.

2. The isolated mutant coryneform bacterium of claim 1, wherein, relative to a bacterial parent strain which does not carry said DNA fragment operably linked to a polynucleotide coding for a protein with dihydrodipicolinate reductase activity, said mutant coryneform bacterium produces at least 0.5% more L-lysine when fermented in nutrient medium and under conditions suitable for lysine production.

3. The isolated mutant coryneform bacterium of claim 1, wherein, relative to a bacterial parent strain which does not carry said DNA fragment operably linked to a polynucleotide coding for a protein with dihydrodipicolinate reductase activity, said mutant coryneform bacterium produces at least 1% more L-lysine when fermented in nutrient medium and under conditions suitable for lysine production.

4. The isolated mutant coryneform bacterium of claim 1, wherein said DNA fragment comprises at least two of said substitutions.

5. The isolated mutant coryneform bacterium of claim 1, wherein said DNA fragment comprises at least three of said substitutions.

6. The isolated mutant coryneform bacterium of claim 1, wherein said DNA fragment comprises all four of said substitutions.

7. The isolated mutant coryneform bacterium of claim 6, wherein, relative to a bacterial parent strain which does not carry said DNA fragment operably linked to a polynucleotide coding for a protein with dihydrodipicolinate reductase activity, said mutant coryneform bacterium produces at least 0.5% more L-lysine when fermented in nutrient medium and under conditions suitable for lysine production.

8. The isolated mutant coryneform bacterium of claim 7, wherein said polynucleotide codes for a polypeptide whose amino acid sequence is at least 90% identical to the amino acid sequence of SEQ ID NO:2.

9. The isolated mutant coryneform bacterium of claim 8, wherein said bacterium is of the species *Corynebacterium glutamicum*.

10. The isolated mutant coryneform bacterium of claim 9, wherein, relative to a bacterial parent strain which does not carry said DNA fragment operably linked to a polynucleotide coding for a protein with dihydrodipicolinate reductase activity, said mutant coryneform bacterium produces at least 1% more L-lysine when fermented in nutrient medium and under conditions suitable for lysine production.

11. The isolated mutant coryneform bacterium of claim 10, wherein, relative to a bacterial parent strain which does not carry said DNA fragment operably linked to a polynucleotide coding for a protein with dihydrodipicolinate reductase activity, said mutant coryneform bacterium produces at least 2% more L-lysine when fermented in nutrient medium and under conditions suitable for lysine production.

12. The isolated mutant coryneform bacterium of claim 11, wherein said DNA fragment comprises all four of said substitutions and, relative to a bacterial parent strain which does not carry said DNA fragment operably linked to a polynucleotide coding for a protein with dihydrodipicolinate reductase activity, said mutant coryneform bacterium has at least 10% more dihydrodipicolinate reductase activity.

13. An isolated mutant of a coryneform bacterium which comprises a DNA fragment with promoter activity, wherein said DNA fragment has the sequence of SEQ ID NO:12 but with all of the following substitutions:
   a) substitution of the nucleobase thymine at position 36 of SEQ ID NO:12 by guanine;
   b) substitution of the nucleobase cytosine at position 37 of SEQ ID NO:12 by guanine;
   c) substitution of the nucleobase guanine at position 40 of SEQ ID NO:12 by thymine;
   d) substitution of the nucleobase cytosine at position 42 of SEQ ID NO:12 by adenine;
and wherein, relative to a DNA fragment comprising the sequence of SEQ ID NO:12 without any of said substitutions, said DNA fragment with said substitutions has increased transcriptional activity.

14. The isolated mutant of a coryneform bacterium of claim 13, wherein relative to a bacterial parent strain which does not carry a DNA fragment comprising the sequence of SEQ ID NO:12 with said substitutions said isolated mutant coryneform bacterium produces more L-lysine when fermented in nutrient medium and under conditions suitable for lysine production.

15. The isolated mutant coryneform bacterium of claim 14, wherein said bacterium is of the species *Corynebacterium glutamicum*.

16. The isolated mutant coryneform bacterium of claim 15, wherein, relative to a bacterial parent strain which does not carry said DNA fragment with said substitutions, said mutant coryneform bacterium produces at least 0.5% more L-lysine when fermented in nutrient medium and under conditions suitable for lysine production.

17. The isolated mutant coryneform bacterium of claim 15, wherein, relative to a bacterial parent strain which does not carry said DNA fragment with said substitutions, said mutant coryneform bacterium produces at least 1% more L-lysine when fermented in nutrient medium and under conditions suitable for lysine production.

18. The isolated mutant coryneform bacterium of claim 15, wherein, relative to a bacterial parent strain which does not carry said DNA fragment with said substitutions, said mutant coryneform bacterium has at least 10% more dihydrodipicolinate reductase activity.

19. The isolated mutant coryneform bacterium of claim 16, wherein said polynucleotide codes for a polypeptide whose amino acid sequence is at least 90% identical to the amino acid sequence of SEQ ID NO:2.

20. A process for the production of L-lysine comprising:
   a) fermenting the isolated mutant coryneform bacterium of claim 13 in a medium to produce a fermentation liquor;
   b) allowing L-lysine to accumulate in said fermentation liquor or in said mutant bacterium;
   c) after step b), collecting or isolating said L-lysine along with >0 to 100% of biomass and/or fermentation liquor constituents.

21. The process claim 20, wherein:
   a) relative to a bacterial parent strain which does not carry a DNA fragment comprising the sequence of SEQ ID NO:12 with said substitutions, said isolated mutant coryneform bacterium produces more L-lysine when fermented in nutrient medium and under conditions suitable for lysine production;
   b) said isolated mutant coryneform bacterium is of the species *Corynebacterium glutamicum*.

22. The process of claim 21, wherein, relative to a bacterial parent strain which does not carry said DNA fragment with said substitutions, said isolated mutant coryneform bacterium produces at least 0.5% more L-lysine.

23. The isolated mutant coryneform bacterium of claim 22, wherein said polynucleotide codes for a polypeptide whose amino acid sequence is at least 90% identical to the amino acid sequence of SEQ ID NO:2.

24. The process of claim 23, wherein, relative to a bacterial parent strain which does not carry said DNA fragment with said substitutions, said isolated mutant coryneform bacterium produces at least 1% more L-lysine.

25. The process of claim 23, wherein, after step b), said L-lysine is purified.

26. The process of claim 23, wherein, after step b), said L lysine together with said fermentation liquor and said biomass are collected.

* * * * *

SEQUENCE LISTING

<160> NUMBER OF SEQ ID NOS: 19

<210> SEQ ID NO 1
<211> LENGTH: 747
<212> TYPE: DNA
<213> ORGANISM: Corynebacterium glutamicum
<220> FEATURE:
<221> NAME/KEY: CDS
<222> LOCATION: (1)..(747)
<223> OTHER INFORMATION: dapB coding region

<400> SEQUENCE: 1

```
atg gga atc aag gtt ggc gtt ctc gga gcc aaa ggc cgt gtt ggt caa         48
Met Gly Ile Lys Val Gly Val Leu Gly Ala Lys Gly Arg Val Gly Gln
1               5                   10                  15 act att gtg gca gca gtc aat gag tcc gac gat ctg gag ctt gtt gca         96
Thr Ile Val Ala Ala Val Asn Glu Ser Asp Asp Leu Glu Leu Val Ala
            20                  25                  30 gag atc ggc gtc gac gat gat ttg agc ctt ctg gta gac aac ggc gct        144
Glu Ile Gly Val Asp Asp Asp Leu Ser Leu Leu Val Asp Asn Gly Ala
        35                  40                  45 gaa gtt gtc gtt gac ttc acc act cct aac gct gtg atg ggc aac ctg        192
Glu Val Val Val Asp Phe Thr Thr Pro Asn Ala Val Met Gly Asn Leu
    50                  55                  60 gag ttc tgc atc aac aac ggc att tct gcg gtt gtt gga acc acg ggc        240
Glu Phe Cys Ile Asn Asn Gly Ile Ser Ala Val Val Gly Thr Thr Gly
65                  70                  75                  80 ttc gat gat gct cgt ttg gag cag gtt cgc gac tgg ctt gaa gga aaa        288
Phe Asp Asp Ala Arg Leu Glu Gln Val Arg Asp Trp Leu Glu Gly Lys
                85                  90                  95 gac aat gtc ggt gtt ctg atc gca cct aac ttt gct atc tct gcg gtg        336
Asp Asn Val Gly Val Leu Ile Ala Pro Asn Phe Ala Ile Ser Ala Val
            100                 105                 110 ttg acc atg gtc ttt tcc aag cag gct gcc cgc ttc ttc gaa tca gct        384
Leu Thr Met Val Phe Ser Lys Gln Ala Ala Arg Phe Phe Glu Ser Ala
        115                 120                 125 gaa gtt att gag ctg cac cac ccc aac aag ctg gat gca cct tca ggc        432
Glu Val Ile Glu Leu His His Pro Asn Lys Leu Asp Ala Pro Ser Gly
    130                 135                 140 acc gcg atc cac act gct cag ggc att gct gcg gca cgc aaa gaa gca        480
Thr Ala Ile His Thr Ala Gln Gly Ile Ala Ala Ala Arg Lys Glu Ala
145                 150                 155                 160 ggc atg gac gca cag cca gat gcg acc gag cag gca ctt gag ggt tcc        528
```

```
            Gly Met Asp Ala Gln Pro Asp Ala Thr Glu Gln Ala Leu Glu Gly Ser
                            165                 170                 175 cgt ggc gca agc gta gat gga atc ccg gtt cat gca gtc cgc atg tcc          576
Arg Gly Ala Ser Val Asp Gly Ile Pro Val His Ala Val Arg Met Ser
                180                 185                 190 ggc atg gtt gct cac gag caa gtt atc ttt ggc acc cag ggt cag acc          624
Gly Met Val Ala His Glu Gln Val Ile Phe Gly Thr Gln Gly Gln Thr
                195                 200                 205 ttg acc atc aag cag gac tcc tat gat cgc aac tca ttt gca cca ggt          672
Leu Thr Ile Lys Gln Asp Ser Tyr Asp Arg Asn Ser Phe Ala Pro Gly
            210                 215                 220 gtc ttg gtg ggt gtg cgc aac att gca cag cac cca ggc cta gtc gta          720
Val Leu Val Gly Val Arg Asn Ile Ala Gln His Pro Gly Leu Val Val
225                 230                 235                 240 gga ctt gag cat tac cta ggc ctg taa                                      747
Gly Leu Glu His Tyr Leu Gly Leu
                245

<210> SEQ ID NO 2
<211> LENGTH: 248
<212> TYPE: PRT
<213> ORGANISM: Corynebacterium glutamicum

<400> SEQUENCE: 2

Met Gly Ile Lys Val Gly Val Leu Gly Ala Lys Gly Arg Val Gly Gln
1               5                   10                  15

Thr Ile Val Ala Ala Val Asn Glu Ser Asp Asp Leu Glu Leu Val Ala
                20                  25                  30

Glu Ile Gly Val Asp Asp Leu Ser Leu Leu Val Asp Asn Gly Ala
            35                  40                  45

Glu Val Val Val Asp Phe Thr Thr Pro Asn Ala Val Met Gly Asn Leu
    50                  55                  60

Glu Phe Cys Ile Asn Asn Gly Ile Ser Ala Val Val Gly Thr Thr Gly
65                  70                  75                  80

Phe Asp Asp Ala Arg Leu Glu Gln Val Arg Asp Trp Leu Glu Gly Lys
                85                  90                  95

Asp Asn Val Gly Val Leu Ile Ala Pro Asn Phe Ala Ile Ser Ala Val
                100                 105                 110

Leu Thr Met Val Phe Ser Lys Gln Ala Ala Arg Phe Phe Glu Ser Ala
            115                 120                 125

Glu Val Ile Glu Leu His His Pro Asn Lys Leu Asp Ala Pro Ser Gly
    130                 135                 140

Thr Ala Ile His Thr Ala Gln Gly Ile Ala Ala Ala Arg Lys Glu Ala
145                 150                 155                 160

Gly Met Asp Ala Gln Pro Asp Ala Thr Glu Gln Ala Leu Glu Gly Ser
                165                 170                 175

Arg Gly Ala Ser Val Asp Gly Ile Pro Val His Ala Val Arg Met Ser
                180                 185                 190

Gly Met Val Ala His Glu Gln Val Ile Phe Gly Thr Gln Gly Gln Thr
            195                 200                 205

Leu Thr Ile Lys Gln Asp Ser Tyr Asp Arg Asn Ser Phe Ala Pro Gly
    210                 215                 220

Val Leu Val Gly Val Arg Asn Ile Ala Gln His Pro Gly Leu Val Val
225                 230                 235                 240

Gly Leu Glu His Tyr Leu Gly Leu
                245
```

-continued

```
<210> SEQ ID NO 3
<211> LENGTH: 2702
<212> TYPE: DNA
<213> ORGANISM: Corynebacterium glutamicum
<220> FEATURE:
<221> NAME/KEY: promoter
<222> LOCATION: (916)..(975)
<223> OTHER INFORMATION: promoter region corresponding to SEQ ID NO: 12
<220> FEATURE:
<221> NAME/KEY: CDS
<222> LOCATION: (1006)..(1752)
<223> OTHER INFORMATION: dapB coding region

<400> SEQUENCE: 3
aagaggacta attagttctg ctagatcgg  gctagatcgg gctaaaaata aatgtggcgc      60
taaaacctta ttgcgaggtt ttagcgccac atttttctat ctgtagttga cggcgttcca    120
gcgctagtga acgatgtcca ccacaagcct ggttggttcc tgcagcaatg agaccgagta    180
atttcggggt tgaccagata caccaatgag aacttgggaa cgggcttcaa aaatactggt    240
gaagttgatg tcttcaacaa tgcctgcacc aggatatgat ccggtatcga tacctggaac    300
gacaacctga tcaggatatc cagtgccttg aatattgacg ttgaggaagg aatcaccagc    360
catctcaact ggaagacctg acgcctgctg aattggatca gtggcccaat cgacccacca    420
accaggttgg ccattaccgg cgatatcaaa acaactcgt gtgaacgttt cgtgctcggc     480
aacgcggatg ccagcgatcg acatatcgga gtcaccaact tgagcctgct gcttctgatc    540
catcgacggg gaacccaacg gcggcaaagc agtgggggaa ggggagttgg tggactctga    600
accagtgggc tctgaagtgg taggcgacgg ggcagcatct gaaggcgtgc gagttgtggt    660
gaccgggtta gcggtttcag tttctgtcac aactggagca ggactagcag aggttgtagg    720
cgttgagccg cttccatcac aagcacttaa agtaaagag gcggaaacca caagcgccaa     780
ggaactacct gcggaacggg cggtgaaggg caacttaagt ctcatatttc aaacatagtt    840
ccacctgtgt gattaatccc tagaacggaa caaactgatg aacaatcgtt aacaacacag    900
accaaaacgg tcagttaggt atggatatca gcaccttctg aacgggtacg tctagactgg    960
tgggcgtttg aaaaactctt cgccccacga aatgaagga gcata atg gga atc aag     1017
                                                  Met Gly Ile Lys
                                                    1 gtt ggc gtt ctc gga gcc aaa ggc cgt gtt ggt caa act att gtg gca     1065
Val Gly Val Leu Gly Ala Lys Gly Arg Val Gly Gln Thr Ile Val Ala
 5                  10                  15                  20 gca gtc aat gag tcc gac gat ctg gag ctt gtt gca gag atc ggc gtc     1113
Ala Val Asn Glu Ser Asp Asp Leu Glu Leu Val Ala Glu Ile Gly Val
                 25                  30                  35 gac gat gat ttg agc ctt ctg gta gac aac ggc gct gaa gtt gtc gtt     1161
Asp Asp Asp Leu Ser Leu Leu Val Asp Asn Gly Ala Glu Val Val Val
             40                  45                  50 gac ttc acc act cct aac gct gtg atg ggc aac ctg gag ttc tgc atc     1209
Asp Phe Thr Thr Pro Asn Ala Val Met Gly Asn Leu Glu Phe Cys Ile
         55                  60                  65 aac aac ggc att tct gcg gtt gtt gga acc acg ggc ttc gat gat gct     1257
Asn Asn Gly Ile Ser Ala Val Val Gly Thr Thr Gly Phe Asp Asp Ala
 70                  75                  80 cgt ttg gag cag gtt cgc gac tgg ctt gaa gga aaa gac aat gtc ggt     1305
Arg Leu Glu Gln Val Arg Asp Trp Leu Glu Gly Lys Asp Asn Val Gly
85                  90                  95                 100 gtt ctg atc gca cct aac ttt gct atc tct gcg gtg ttg acc atg gtc     1353
Val Leu Ile Ala Pro Asn Phe Ala Ile Ser Ala Val Leu Thr Met Val
                105                 110                 115 ttt tcc aag cag gct gcc cgc ttc ttc gaa tca gct gaa gtt att gag     1401
```

```
                    Phe Ser Lys Gln Ala Ala Arg Phe Phe Glu Ser Ala Glu Val Ile Glu
                                    120                 125                 130 ctg cac cac ccc aac aag ctg gat gca cct tca ggc acc gcg atc cac                1449
Leu His His Pro Asn Lys Leu Asp Ala Pro Ser Gly Thr Ala Ile His
            135                 140                 145 act gct cag ggc att gct gcg gca cgc aaa gaa gca ggc atg gac gca                1497
Thr Ala Gln Gly Ile Ala Ala Ala Arg Lys Glu Ala Gly Met Asp Ala
150                 155                 160 cag cca gat gcg acc gag cag gca ctt gag ggt tcc cgt ggc gca agc                1545
Gln Pro Asp Ala Thr Glu Gln Ala Leu Glu Gly Ser Arg Gly Ala Ser
165                 170                 175                 180 gta gat gga atc ccg gtt cat gca gtc cgc atg tcc ggc atg gtt gct                1593
Val Asp Gly Ile Pro Val His Ala Val Arg Met Ser Gly Met Val Ala
                185                 190                 195 cac gag caa gtt atc ttt ggc acc cag ggt cag acc ttg acc atc aag                1641
His Glu Gln Val Ile Phe Gly Thr Gln Gly Gln Thr Leu Thr Ile Lys
            200                 205                 210 cag gac tcc tat gat cgc aac tca ttt gca cca ggt gtc ttg gtg ggt                1689
Gln Asp Ser Tyr Asp Arg Asn Ser Phe Ala Pro Gly Val Leu Val Gly
        215                 220                 225 gtg cgc aac att gca cag cac cca ggc cta gtc gta gga ctt gag cat                1737
Val Arg Asn Ile Ala Gln His Pro Gly Leu Val Val Gly Leu Glu His
    230                 235                 240 tac cta ggc ctg taa aggctcattt cagcagcggg tggaattttt taaaaggagc                1792
Tyr Leu Gly Leu
245 gtttaaaggc tgtggccgaa caagttaaat tgagcgtgga gttgatagcg tgcagttctt              1852 ttactccacc cgctgatgtt gagtggtcaa ctgatgttga gggcgcggaa gcactcgtcg              1912 agtttgcggg tcgtgcctgc tacgaaactt ttgataagcc gaaccctcga actgcttcca              1972 atgctgcgta tctgcgccac atcatggaag tggggcacac tgctttgctt gagcatgcca              2032 atgccacgat gtatatccga ggcatttctc ggtccgcgac ccatgaattg gtccgacacc              2092 gccattttc cttctctcaa ctgtctcagc gttttcgtgca cagcggagaa tcggaagtag              2152 tggtgcccac tctcatcgat gaagatccgc agttgcgtga acttttcatg cacgccatgg              2212 atgagtctcg gttcgctttc aatgagctgc ttaatgcgct ggaagaaaaa cttggcgatg              2272 aaccgaatgc acttttaagg aaaaagcagg ctcgtcaagc agctcgcgct gtgctgccca              2332 acgctacaga gtccagaatc gtggtgtctg gaaacttccg cacctggagg catttcattg              2392 gcatgcgagc cagtgaacat gcagacgtcg aaatccgcga agtagcggta gaatgtttaa              2452 gaaagctgca ggtagcagcg ccaactgttt tcggtgattt tgagattgaa actttggcag              2512 acggatcgca aatggcaaca agcccgtatg tcatggactt taacgcaaa gctcacaccc               2572 acgagctaaa aattcatata gttaagacaa catttttggc tgtaaaagac agccgtaaaa              2632 acctcttgct cgtgtcaatt gttcttatcg gaatgtggct tgggcgattg ttatgcaaaa              2692 gttgttaggt                                                                    2702

<210> SEQ ID NO 4
<211> LENGTH: 248
<212> TYPE: PRT
<213> ORGANISM: Corynebacterium glutamicum

<400> SEQUENCE: 4

Met Gly Ile Lys Val Gly Val Leu Gly Ala Lys Gly Arg Val Gly Gln
1               5                   10                  15

Thr Ile Val Ala Ala Val Asn Glu Ser Asp Asp Leu Glu Leu Val Ala
                20                  25                  30
```

```
Glu Ile Gly Val Asp Asp Leu Ser Leu Leu Val Asp Asn Gly Ala
            35                  40                  45

Glu Val Val Asp Phe Thr Thr Pro Asn Ala Val Met Gly Asn Leu
 50                  55                  60

Glu Phe Cys Ile Asn Asn Gly Ile Ser Ala Val Val Gly Thr Thr Gly
 65                  70                  75                  80

Phe Asp Asp Ala Arg Leu Glu Gln Val Arg Asp Trp Leu Glu Gly Lys
                 85                  90                  95

Asp Asn Val Gly Val Leu Ile Ala Pro Asn Phe Ala Ile Ser Ala Val
                100                 105                 110

Leu Thr Met Val Phe Ser Lys Gln Ala Ala Arg Phe Phe Glu Ser Ala
            115                 120                 125

Glu Val Ile Glu Leu His His Pro Asn Lys Leu Asp Ala Pro Ser Gly
        130                 135                 140

Thr Ala Ile His Thr Ala Gln Gly Ile Ala Ala Arg Lys Glu Ala
145                 150                 155                 160

Gly Met Asp Ala Gln Pro Asp Ala Thr Glu Gln Ala Leu Glu Gly Ser
                165                 170                 175

Arg Gly Ala Ser Val Asp Gly Ile Pro Val His Ala Val Arg Met Ser
            180                 185                 190

Gly Met Val Ala His Glu Gln Val Ile Phe Gly Thr Gln Gly Gln Thr
        195                 200                 205

Leu Thr Ile Lys Gln Asp Ser Tyr Asp Arg Asn Ser Phe Ala Pro Gly
    210                 215                 220

Val Leu Val Gly Val Arg Asn Ile Ala Gln His Pro Gly Leu Val Val
225                 230                 235                 240

Gly Leu Glu His Tyr Leu Gly Leu
                245

<210> SEQ ID NO 5
<211> LENGTH: 1690
<212> TYPE: DNA
<213> ORGANISM: Corynebacterium glutamicum
<220> FEATURE:
<221> NAME/KEY: promoter
<222> LOCATION: (823)..(882)
<223> OTHER INFORMATION: promoter region corresponding to SEQ ID NO: 13
<220> FEATURE:
<221> NAME/KEY: mutation
<222> LOCATION: (858)..(858)
<223> OTHER INFORMATION: t-to-g transversion at position -55
<220> FEATURE:
<221> NAME/KEY: mutation
<222> LOCATION: (859)..(859)
<223> OTHER INFORMATION: c-to-g transversion at position -54
<220> FEATURE:
<221> NAME/KEY: mutation
<222> LOCATION: (862)..(862)
<223> OTHER INFORMATION: g-to-t transversion at position -51
<220> FEATURE:
<221> NAME/KEY: mutation
<222> LOCATION: (864)..(864)
<223> OTHER INFORMATION: c-to-a transversion at position -49
<220> FEATURE:
<221> NAME/KEY: CDS
<222> LOCATION: (913)..(1659)
<223> OTHER INFORMATION: dapB coding region

<400> SEQUENCE: 5
ccgaattctg tagttgacgg cgttccagcg ctagtgaacg atgtccacca caagcctggt      60
tggttcctgc agcaatgaga ccgagtaatt tcggggttga ccagatacac caatgagaac     120
ttgggaacgg gcttcaaaaa tactggtgaa gttgatgtct tcaacaatgc ctgcaccagg     180
```

```
atatgatccg gtatcgatac ctggaacgac aacctgatca ggatatccag tgccttgaat      240
attgacgttg aggaaggaat caccagccat ctcaactgga agacctgacg cctgctgaat      300
tggatcagtg gcccaatcga cccaccaacc aggttggcca ttaccggcga tatcaaaaac      360
aactcgtgtg aacgtttcgt gctcggcaac gcggatgcca gcgatcgaca tatcggagtc      420
accaacttga gcctgctgct tctgatccat cgacggggaa cccaacgcg gcaaagcagt       480 gggggaaggg gagttggtgg actctgaacc agtgggctct gaagtggtag cgacggggc      540 agcatctgaa ggcgtgcgag ttgtggtgac cgggttagcg gtttcagttt ctgtcacaac      600
tggagcagga ctagcagagg ttgtaggcgt tgagccgctt ccatcacaag cacttaaaag      660
taaagaggcg gaaaccacaa gcgccaagga actacctgcg gaacgggcgg tgaagggcaa      720
cttaagtctc atatttcaaa catagttcca cctgtgtgat taatccctag aacgaacaa       780 actgatgaac aatcgttaac aacacagacc aaaacggtca gttaggtatg gatatcagca      840
ccttctgaac gggtacgggt ataatggtgg gcgtttgaaa aactcttcgc cccacgaaaa      900
tgaaggagca ta atg gga atc aag gtt ggc gtt ctc gga gcc aaa ggc cgt      951
              Met Gly Ile Lys Val Gly Val Leu Gly Ala Lys Gly Arg
                1               5                  10 gtt ggt caa act att gtg gca gca gtc aat gag tcc gac gat ctg gag       999
Val Gly Gln Thr Ile Val Ala Ala Val Asn Glu Ser Asp Asp Leu Glu
     15                  20                  25 ctt gtt gca gag atc ggc gtc gac gat gat ttg agc ctt ctg gta gac      1047
Leu Val Ala Glu Ile Gly Val Asp Asp Asp Leu Ser Leu Leu Val Asp
30                  35                  40                  45 aac ggc gct gaa gtt gtc gtt gac ttc acc act cct aac gct gtg atg      1095
Asn Gly Ala Glu Val Val Val Asp Phe Thr Thr Pro Asn Ala Val Met
                 50                  55                  60 ggc aac ctg gag ttc tgc atc aac aac ggc att tct gcg gtt gtt gga      1143
Gly Asn Leu Glu Phe Cys Ile Asn Asn Gly Ile Ser Ala Val Val Gly
             65                  70                  75 acc acg ggc ttc gat gat gct cgt ttg gag cag gtt cgc gac tgg ctt      1191
Thr Thr Gly Phe Asp Asp Ala Arg Leu Glu Gln Val Arg Asp Trp Leu
         80                  85                  90 gaa gga aaa gac aat gtc ggt gtt ctg atc gca cct aac ttt gct atc      1239
Glu Gly Lys Asp Asn Val Gly Val Leu Ile Ala Pro Asn Phe Ala Ile
     95                 100                 105 tct gcg gtg ttg acc atg gtc ttt tcc aag cag gct gcc cgc ttc ttc      1287
Ser Ala Val Leu Thr Met Val Phe Ser Lys Gln Ala Ala Arg Phe Phe
110                 115                 120                 125 gaa tca gct gaa gtt att gag ctg cac cac ccc aac aag ctg gat gca      1335
Glu Ser Ala Glu Val Ile Glu Leu His His Pro Asn Lys Leu Asp Ala
                130                 135                 140 cct tca ggc acc gcg atc cac act gct cag ggc att gct gcg gca cgc      1383
Pro Ser Gly Thr Ala Ile His Thr Ala Gln Gly Ile Ala Ala Ala Arg
            145                 150                 155 aaa gaa gca ggc atg gac gca cag cca gat gcg acc gag cag gca ctt      1431
Lys Glu Ala Gly Met Asp Ala Gln Pro Asp Ala Thr Glu Gln Ala Leu
        160                 165                 170 gag ggt tcc cgt ggc gca agc gta gat gga atc ccg gtt cat gca gtc      1479
Glu Gly Ser Arg Gly Ala Ser Val Asp Gly Ile Pro Val His Ala Val
    175                 180                 185 cgc atg tcc ggc atg gtt gct cac gag caa gtt atc ttt ggc acc cag      1527
Arg Met Ser Gly Met Val Ala His Glu Gln Val Ile Phe Gly Thr Gln
190                 195                 200                 205 ggt cag acc ttg acc atc aag cag gac tcc tat gat cgc aac tca ttt      1575
Gly Gln Thr Leu Thr Ile Lys Gln Asp Ser Tyr Asp Arg Asn Ser Phe
                210                 215                 220
```

```
gca cca ggt gtc ttg gtg ggt gtg cgc aac att gca cag cac cca ggc    1623
Ala Pro Gly Val Leu Val Gly Val Arg Asn Ile Ala Gln His Pro Gly
            225                 230                 235 cta gtc gta gga ctt gag cat tac cta ggc ctg taa aggctcattt         1669
Leu Val Val Gly Leu Glu His Tyr Leu Gly Leu
        240                 245 cagcagcggg tggaagcttg g                                             1690
```

<210> SEQ ID NO 6
<211> LENGTH: 248
<212> TYPE: PRT
<213> ORGANISM: Corynebacterium glutamicum

<400> SEQUENCE: 6

```
Met Gly Ile Lys Val Gly Val Leu Gly Ala Lys Gly Arg Val Gly Gln
1               5                   10                  15

Thr Ile Val Ala Ala Val Asn Glu Ser Asp Asp Leu Glu Leu Val Ala
            20                  25                  30

Glu Ile Gly Val Asp Asp Leu Ser Leu Leu Val Asp Asn Gly Ala
        35                  40                  45

Glu Val Val Asp Phe Thr Thr Pro Asn Ala Val Met Gly Asn Leu
    50                  55                  60

Glu Phe Cys Ile Asn Asn Gly Ile Ser Ala Val Val Gly Thr Thr Gly
65                  70                  75                  80

Phe Asp Asp Ala Arg Leu Glu Gln Val Arg Asp Trp Leu Glu Gly Lys
                85                  90                  95

Asp Asn Val Gly Val Leu Ile Ala Pro Asn Phe Ala Ile Ser Ala Val
            100                 105                 110

Leu Thr Met Val Phe Ser Lys Gln Ala Ala Arg Phe Phe Glu Ser Ala
        115                 120                 125

Glu Val Ile Glu Leu His His Pro Asn Lys Leu Asp Ala Pro Ser Gly
    130                 135                 140

Thr Ala Ile His Thr Ala Gln Gly Ile Ala Ala Ala Arg Lys Glu Ala
145                 150                 155                 160

Gly Met Asp Ala Gln Pro Asp Ala Thr Glu Gln Ala Leu Glu Gly Ser
                165                 170                 175

Arg Gly Ala Ser Val Asp Gly Ile Pro Val His Ala Val Arg Met Ser
            180                 185                 190

Gly Met Val Ala His Glu Gln Val Ile Phe Gly Thr Gln Gly Gln Thr
        195                 200                 205

Leu Thr Ile Lys Gln Asp Ser Tyr Asp Arg Asn Ser Phe Ala Pro Gly
    210                 215                 220

Val Leu Val Gly Val Arg Asn Ile Ala Gln His Pro Gly Leu Val Val
225                 230                 235                 240

Gly Leu Glu His Tyr Leu Gly Leu
                245
```

<210> SEQ ID NO 7
<211> LENGTH: 26
<212> TYPE: DNA
<213> ORGANISM: Corynebacterium glutamicum
<220> FEATURE:
<221> NAME/KEY: misc_feature
<222> LOCATION: (1)..(26)
<223> OTHER INFORMATION: Primer PdapBN1_1.p

<400> SEQUENCE: 7

```
ccgaattctg tagttgacgg cgttcc                                        26
```

```
<210> SEQ ID NO 8
<211> LENGTH: 26
<212> TYPE: DNA
<213> ORGANISM: Corynebacterium glutamicum
<220> FEATURE:
<221> NAME/KEY: misc_feature
<222> LOCATION: (1)..(26)
<223> OTHER INFORMATION: Primer PdapBN1_4.p

<400> SEQUENCE: 8
ccaagcttcc acccgctgct gaaatg                                        26

<210> SEQ ID NO 9
<211> LENGTH: 100
<212> TYPE: DNA
<213> ORGANISM: Corynebacterium glutamicum
<220> FEATURE:
<221> NAME/KEY: -10_signal
<222> LOCATION: (48)..(53)
<223> OTHER INFORMATION: P1 -10

<400> SEQUENCE: 9
aacggtcagt taggtatgga tatcagcacc ttctgaacgg gtacgtctag actggtgggc    60
gtttgaaaaa ctcttcgccc cacgaaaatg aaggagcata                        100

<210> SEQ ID NO 10
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer dapB_P_A1

<400> SEQUENCE: 10
ccctagaacg gaacaaactg                                               20

<210> SEQ ID NO 11
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer dapB_P_E1

<400> SEQUENCE: 11
agaacgccaa ccttgattcc                                               20

<210> SEQ ID NO 12
<211> LENGTH: 60
<212> TYPE: DNA
<213> ORGANISM: Corynebacterium glutamicum
<220> FEATURE:
<221> NAME/KEY: -35_signal
<222> LOCATION: (14)..(19)
<220> FEATURE:
<221> NAME/KEY: -10_signal
<222> LOCATION: (38)..(43)

<400> SEQUENCE: 12
taggtatgga tatcagcacc ttctgaacgg gtacgtctag actggtgggc gtttgaaaaa    60

<210> SEQ ID NO 13
<211> LENGTH: 60
<212> TYPE: DNA
<213> ORGANISM: Corynebacterium glutamicum
```

```
<220> FEATURE:
<221> NAME/KEY: -35_signal
<222> LOCATION: (14)..(19)
<220> FEATURE:
<221> NAME/KEY: mutation
<222> LOCATION: (36)..(36)
<223> OTHER INFORMATION: t-to-g transversion
<220> FEATURE:
<221> NAME/KEY: mutation
<222> LOCATION: (37)..(37)
<223> OTHER INFORMATION: c-to-g transversion
<220> FEATURE:
<221> NAME/KEY: -10_signal
<222> LOCATION: (38)..(43)
<220> FEATURE:
<221> NAME/KEY: mutation
<222> LOCATION: (40)..(40)
<223> OTHER INFORMATION: g-to-t transversion
<220> FEATURE:
<221> NAME/KEY: mutation
<222> LOCATION: (42)..(42)
<223> OTHER INFORMATION: c-to-a transversion

<400> SEQUENCE: 13
taggtatgga tatcagcacc ttctgaacgg gtacgggtat aatggtgggc gtttgaaaaa      60

<210> SEQ ID NO 14
<211> LENGTH: 1266
<212> TYPE: DNA
<213> ORGANISM: Corynebacterium glutamicum
<220> FEATURE:
<221> NAME/KEY: CDS
<222> LOCATION: (1)..(1263)
<223> OTHER INFORMATION: lysC wild-type gene

<400> SEQUENCE: 14 gtg gcc ctg gtc gta cag aaa tat ggc ggt tcc tcg ctt gag agt gcg      48
Val Ala Leu Val Val Gln Lys Tyr Gly Gly Ser Ser Leu Glu Ser Ala
1               5                   10                  15 gaa cgc att aga aac gtc gct gaa cgg atc gtt gcc acc aag aag gct      96
Glu Arg Ile Arg Asn Val Ala Glu Arg Ile Val Ala Thr Lys Lys Ala
            20                  25                  30 gga aat gat gtc gtg gtt gtc tgc tcc gca atg gga gac acc acg gat     144
Gly Asn Asp Val Val Val Val Cys Ser Ala Met Gly Asp Thr Thr Asp
        35                  40                  45 gaa ctt cta gaa ctt gca gcg gca gtg aat ccc gtt ccg cca gct cgt     192
Glu Leu Leu Glu Leu Ala Ala Ala Val Asn Pro Val Pro Pro Ala Arg
    50                  55                  60 gaa atg gat atg ctc ctg act gct ggt gag cgt att tct aac gct ctc     240
Glu Met Asp Met Leu Leu Thr Ala Gly Glu Arg Ile Ser Asn Ala Leu
65                  70                  75                  80 gtc gcc atg gct att gag tcc ctt ggc gca gaa gcc caa tct ttc acg     288
Val Ala Met Ala Ile Glu Ser Leu Gly Ala Glu Ala Gln Ser Phe Thr
                85                  90                  95 ggc tct cag gct ggt gtg ctc acc acc gag cgc cac gga aac gca cgc     336
Gly Ser Gln Ala Gly Val Leu Thr Thr Glu Arg His Gly Asn Ala Arg
            100                 105                 110 att gtt gat gtc act cca ggt cgt gtg cgt gaa gca ctc gat gag ggc     384
Ile Val Asp Val Thr Pro Gly Arg Val Arg Glu Ala Leu Asp Glu Gly
        115                 120                 125 aag atc tgc att gtt gct ggt ttc cag ggt gtt aat aaa gaa acc cgc     432
Lys Ile Cys Ile Val Ala Gly Phe Gln Gly Val Asn Lys Glu Thr Arg
    130                 135                 140 gat gtc acc acg ttg ggt cgt ggt ggt tct gac acc act gca gtt gcg     480
Asp Val Thr Thr Leu Gly Arg Gly Gly Ser Asp Thr Thr Ala Val Ala
145                 150                 155                 160 ttg gca gct gct ttg aac gct gat gtg tgt gag att tac tcg gac gtt     528
```

```
                Leu Ala Ala Ala Leu Asn Ala Asp Val Cys Glu Ile Tyr Ser Asp Val
                                165                 170                 175 gac ggt gtg tat acc gct gac ccg cgc atc gtt cct aat gca cag aag          576
Asp Gly Val Tyr Thr Ala Asp Pro Arg Ile Val Pro Asn Ala Gln Lys
            180                 185                 190 ctg gaa aag ctc agc ttc gaa gaa atg ctg gaa ctt gct gct gtt ggc          624
Leu Glu Lys Leu Ser Phe Glu Glu Met Leu Glu Leu Ala Ala Val Gly
            195                 200                 205 tcc aag att ttg gtg ctg cgc agt gtt gaa tac gct cgt gca ttc aat          672
Ser Lys Ile Leu Val Leu Arg Ser Val Glu Tyr Ala Arg Ala Phe Asn
        210                 215                 220 gtg cca ctt cgc gta cgc tcg tct tat agt aat gat ccc ggc act ttg          720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ctt acc          768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att          816
Gly Val Ala Thr Asp Lys Ser Glu Ala Lys Val Thr Val Leu Gly Ile
                260                 265                 270 tcc gat aag cca ggc gag gct gcg aag gtt ttc cgt gcg ttg gct gat          864
Ser Asp Lys Pro Gly Glu Ala Ala Lys Val Phe Arg Ala Leu Ala Asp
            275                 280                 285 gca gaa atc aac att gac atg gtt ctg cag aac gtc tct tct gta gaa          912
Ala Glu Ile Asn Ile Asp Met Val Leu Gln Asn Val Ser Ser Val Glu
        290                 295                 300 gac ggc acc acc gac atc acc ttc acc tgc cct cgt tcc gac ggc cgc          960
Asp Gly Thr Thr Asp Ile Thr Phe Thr Cys Pro Arg Ser Asp Gly Arg
305                 310                 315                 320 cgc gcg atg gag atc ttg aag aag ctt cag gtt cag ggc aac tgg acc         1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct         1056
Asn Val Leu Tyr Asp Asp Gln Val Gly Lys Val Ser Leu Val Gly Ala
                340                 345                 350 ggc atg aag tct cac cca ggt gtt acc gca gag ttc atg gaa gct ctg         1104
Gly Met Lys Ser His Pro Gly Val Thr Ala Glu Phe Met Glu Ala Leu
            355                 360                 365 cgc gat gtc aac gtg aac atc gaa ttg att tcc acc tct gag att cgt         1152
Arg Asp Val Asn Val Asn Ile Glu Leu Ile Ser Thr Ser Glu Ile Arg
        370                 375                 380 att tcc gtg ctg atc cgt gaa gat gat ctg gat gct gct gca cgt gca         1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat         1248
Leu His Glu Gln Phe Gln Leu Gly Gly Glu Asp Glu Ala Val Val Tyr
                405                 410                 415 gca ggc acc gga cgc taa                                                 1266
Ala Gly Thr Gly Arg
            420

<210> SEQ ID NO 15
<211> LENGTH: 421
<212> TYPE: PRT
<213> ORGANISM: Corynebacterium glutamicum

<400> SEQUENCE: 15

Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30
```

Gly Asn Asp Val Val Val Cys Ser Ala Met Gly Asp Thr Thr Asp
            35                  40                  45

Glu Leu Leu Glu Leu Ala Ala Ala Val Asn Pro Val Pro Pro Ala Arg
 50                  55                  60

Glu Met Asp Met Leu Leu Thr Ala Gly Glu Arg Ile Ser Asn Ala Leu
 65                  70                  75                  80

Val Ala Met Ala Ile Glu Ser Leu Gly Ala Glu Ala Gln Ser Phe Thr
                 85                  90                  95

Gly Ser Gln Ala Gly Val Leu Thr Thr Glu Arg His Gly Asn Ala Arg
                100                 105                 110

Ile Val Asp Val Thr Pro Gly Arg Val Arg Glu Ala Leu Asp Glu Gly
                115                 120                 125

Lys Ile Cys Ile Val Ala Gly Phe Gln Gly Val Asn Lys Glu Thr Arg
            130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
                180                 185                 190

Leu Glu Lys Leu Ser Phe Glu Glu Met Leu Glu Leu Ala Ala Val Gly
                195                 200                 205

Ser Lys Ile Leu Val Leu Arg Ser Val Glu Tyr Ala Arg Ala Phe Asn
            210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
                260                 265                 270

Ser Asp Lys Pro Gly Glu Ala Ala Lys Val Phe Arg Ala Leu Ala Asp
            275                 280                 285

Ala Glu Ile Asn Ile Asp Met Val Leu Gln Asn Val Ser Ser Val Glu
 290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
                340                 345                 350

Gly Met Lys Ser His Pro Gly Val Thr Ala Glu Phe Met Glu Ala Leu
            355                 360                 365

Arg Asp Val Asn Val Asn Ile Glu Leu Ile Ser Thr Ser Glu Ile Arg
 370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 16
<211> LENGTH: 22
<212> TYPE: PRT

```
<213> ORGANISM: Artificial Sequence
<220> FEATURE:
<223> OTHER INFORMATION: Sequence motif found in several different
      bacteria including Mycobacterium tuberculosis, Bifidobacterium
      longum, Streptomyces coelicolor, Corynebacterium efficiens,
      Corynebacterium jeikeium, Corynebacterium glutamicum R and
      Corynebacterium glutamicum
<220> FEATURE:
<221> NAME/KEY: MISC_FEATURE
<222> LOCATION: (2)..(2)
<223> OTHER INFORMATION: X is Asp or Glu
<220> FEATURE:
<221> NAME/KEY: MISC_FEATURE
<222> LOCATION: (4)..(4)
<223> OTHER INFORMATION: X is Ala or Val
<220> FEATURE:
<221> NAME/KEY: MISC_FEATURE
<222> LOCATION: (7)..(7)
<223> OTHER INFORMATION: X is Ile or Val
<220> FEATURE:
<221> NAME/KEY: MISC_FEATURE
<222> LOCATION: (13)..(13)
<223> OTHER INFORMATION: X is Asn, Thr or His
<220> FEATURE:
<221> NAME/KEY: MISC_FEATURE
<222> LOCATION: (15)..(15)
<223> OTHER INFORMATION: X is Val, Leu or Ala

<400> SEQUENCE: 16

Phe Xaa Ser Xaa Glu Val Xaa Glu Leu His His Pro Xaa Lys Xaa Asp
1               5                   10                  15

Ala Pro Ser Gly Thr Ala
            20

<210> SEQ ID NO 17
<211> LENGTH: 11
<212> TYPE: PRT
<213> ORGANISM: Artificial Sequence
<220> FEATURE:
<223> OTHER INFORMATION: Sequence motif found in several different
      bacteria including Mycobacterium tuberculosis, Bifidobacterium
      longum, Streptomyces coelicolor, Corynebacterium efficiens,
      Corynebacterium jeikeium, Corynebacterium glutamicum R and
      Corynebacterium glutamicum
<220> FEATURE:
<221> NAME/KEY: MISC_FEATURE
<222> LOCATION: (2)..(2)
<223> OTHER INFORMATION: X is Asp or Gln
<220> FEATURE:
<221> NAME/KEY: MISC_FEATURE
<222> LOCATION: (4)..(4)
<223> OTHER INFORMATION: X is Ile or Val
<220> FEATURE:
<221> NAME/KEY: MISC_FEATURE
<222> LOCATION: (5)..(5)
<223> OTHER INFORMATION: X is Pro or His
<220> FEATURE:
<221> NAME/KEY: MISC_FEATURE
<222> LOCATION: (11)..(11)
<223> OTHER INFORMATION: X is Leu or Met

<400> SEQUENCE: 17

Val Xaa Gly Xaa Xaa Val His Ala Val Arg Xaa
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Sequence motif found in several different
      bacteria including Mycobacterium tuberculosis, Bifidobacterium
      longum, Streptomyces coelicolor, Corynebacterium efficiens,
      Corynebacterium jeikeium, Corynebacterium glutamicum R and
      Corynebacterium glutamicum
```

```
<220> FEATURE:
<221> NAME/KEY: MISC_FEATURE
<222> LOCATION: (2)..(2)
<223> OTHER INFORMATION: X is Leu or Phe
<220> FEATURE:
<221> NAME/KEY: MISC_FEATURE
<222> LOCATION: (3)..(3)
<223> OTHER INFORMATION: X is Ile or Val
<220> FEATURE:
<221> NAME/KEY: MISC_FEATURE
<222> LOCATION: (8)..(8)
<223> OTHER INFORMATION: X is Ala or Ser
<220> FEATURE:
<221> NAME/KEY: MISC_FEATURE
<222> LOCATION: (10)..(10)
<223> OTHER INFORMATION: X is Ser or Gly

<400> SEQUENCE: 18

Val Xaa Xaa Ala Pro Asn Phe Xaa Ile Xaa Ala Val Leu
1               5                   10

<210> SEQ ID NO 19
<211> LENGTH: 20
<212> TYPE: DNA
<213> ORGANISM: Corynebacterium glutamicum

<400> SEQUENCE: 19
ggtgaagggc aacttaagtc                                                      20
```